US009556154B2

(12) United States Patent
Hu et al.

(10) Patent No.: US 9,556,154 B2
(45) Date of Patent: Jan. 31, 2017

(54) PYRROLE-SUBSTITUTED INDOLONE DERIVATIVE, PREPARATION METHOD THEREFOR, COMPOSITION COMPRISING SAME AND USE THEREOF

(71) Applicant: SHIJIAZHUANG YILING PHARMACEUTICAL CO., LTD., Shijiazhuang, Hebei (CN)

(72) Inventors: Lihong Hu, Shijiazhuang (CN); Shaohua Zhao, Shijiazhuang (CN); Peng Liu, Shijiazhuang (CN); Xiangjun Li, Shijiazhuang (CN); Junyong An, Shijiazhuang (CN); Mengxia Zhou, Shijiazhuang (CN); Lili Zhang, Shijiazhuang (CN); Zijian Yao, Shijiazhuang (CN)

(73) Assignee: Shijiazhuang Yiling Pharmaceutical Co. Ltd. (CN)

( * ) Notice: Subject to any disclaimer, the term of this patent is extended or adjusted under 35 U.S.C. 154(b) by 0 days.

(21) Appl. No.: 15/117,400

(22) PCT Filed: Feb. 4, 2015

(86) PCT No.: PCT/CN2015/072230
§ 371 (c)(1),
(2) Date: Aug. 8, 2016

(87) PCT Pub. No.: WO2015/117551
PCT Pub. Date: Aug. 13, 2015

(65) Prior Publication Data

US 2016/0347740 A1 Dec. 1, 2016

(30) Foreign Application Priority Data

Feb. 10, 2014 (CN) .......................... 2014 1 0046278

(51) Int. Cl.
*C07D 403/14* (2006.01)
*C07D 401/14* (2006.01)
*A61K 31/454* (2006.01)
*A61K 31/404* (2006.01)

(52) U.S. Cl.
CPC ........... *C07D 403/14* (2013.01); *A61K 31/404* (2013.01); *A61K 31/454* (2013.01); *C07D 401/14* (2013.01)

(58) Field of Classification Search
None
See application file for complete search history.

(56) References Cited

U.S. PATENT DOCUMENTS 6,573,293 B2 6/2003 Tang et al.
7,125,905 B2 10/2006 Tang et al.
7,572,924 B2 8/2009 Tang et al.

FOREIGN PATENT DOCUMENTS

WO WO 2007 085205 A1 8/2007

OTHER PUBLICATIONS

Database CAPLUS in STN, Acc. No. 2007:845191, Deng et al., WO2007/085205 A1 (Aug. 2, 2007) (abstract).*

* cited by examiner

*Primary Examiner* — Brian J Davis
(74) *Attorney, Agent, or Firm* — Foley & Lardner LLP

(57) ABSTRACT

The present invention relates to a pyrrole-substituted indolone derivative, a preparation method therefor, a composition comprising the derivative, and use thereof. The pyrrole-substituted indolone derivative has a structure shown in formula (I) below. The present invention further relates to use of the pyrrole-substituted indolone derivative for treating receptor tyrosine kinase-mediated diseases, and to a pharmaceutical composition comprising compounds having such a structure for treating related diseases such as tumors.

(I)

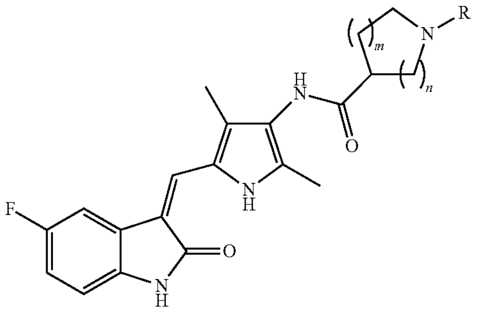

20 Claims, No Drawings

PYRROLE-SUBSTITUTED INDOLONE DERIVATIVE, PREPARATION METHOD THEREFOR, COMPOSITION COMPRISING SAME AND USE THEREOF

TECHNICAL FIELD

The present invention relates to a pyrrole-substituted indolone derivative or pharmaceutically acceptable salts thereof, a preparation method therefor, a composition comprising the same and use thereof. In particular, the present invention relates to a pyrrole-substituted indolone derivative as a multi-target tyrosine kinase inhibitor, a pharmaceutical composition comprising the derivative, and their medical use.

BACKGROUND ART

Cancer has become the disease that poses the biggest threat to health of human beings in modern society. To date, many anti-cancer drugs available in the market are still cytotoxic drugs discovered in the last century, which kill a vast number of normal cells during tumor treatment, causing intolerable side effects to patients, and another intractable problem of drug resistance comes up as these drugs are extensively used.

Tumor vessel inhibition represents a new method developed in the late stage of last century for tumor treatment, and its research was based on the theory proposed by Folkman that survival, growth and metastasis of tumors rely on an extensive network of neovessels (Folkman. J. et. al. N. Engl. J. Med., 1971, 285, 1182-1186). It has been found in a large amount of clinical research that tumor tissues contain many neovessels, and growth and metastasis of tumor cells require a large number of vessels to supply sufficient oxygen and nutrients. Inhibition of neoangiogenesis in tumors can "starve" tumor cells to death, while inhibition of neovessels have little impact on normal cells because there are very few neovessels around normal cells which results in vessel inhibition-based anti-tumor drugs having characteristics such as high efficiency, safety and low toxicity.

Vessel inhibition may be classified into direct inhibition and indirect inhibition. Direct inhibition is an action on vascular endothelial cells to inhibit angiogenesis, extension and nutritional support to tumor cells of vessels. The main method currently used here is metronomic therapy with a cytotoxic drug, which can mitigate side effects of the cytotoxic drug but has difficulty in improving the damage caused by the drug to human bodies. Indirect inhibition suppresses neoangiogenesis by inhibiting angiogenic factors required for angiogenesis (Cao, Y. et. al. Int. J. Biochem. Cell Biol., 2001, 33, 357-369.). The process of angiogenesis includes activation of vascular endothelial cells under the action of an activator; secretion of proteases from the endothelial cells to degrade the basal membrane; migration and proliferation of the endothelial cells; formation of the lumen of neo-capillaries; and recruitment of pericytes to stabilize the peripheral structure of the neo-capillaries. Under physiological conditions there are two kinds of factors acting on angiogenesis, namely angiogenesis inhibitors and pro-angiogenic factors. Angiogenesis inhibitors may be categorized into two major types according to their functional specificity: one type is angiogenesis inhibitors specifically acting on endothelial cells, including angiostatins, endostatins and the like; and the other type is angiogenesis inhibitors non-specifically acting on endothelial cells, including cytokines, tissue metalloproteinase inhibitors, serine protease inhibitors, tumor suppressor gene products and the like. Pro-angiogenic factors include epidermal growth factor (EGF), vascular endothelial growth factor (VEGF), platelet derived growth factor (PDGF), fibroblast growth factor (FGF) and the like (Hanks, S. K., et. al. FASEB, 1995, 9, 576-696). High-level expressions of various pro-angiogenic factors can be seen in different types of tumors, such as a high-level expression of EGF typically seen in epithelial cell tumors, and a high-level expression of PDGF typically seen in glioma. Current strategies for developing an anti-cancer drug against the tumor neoangiogenesis pathway mainly focus on increase in angiogenesis inhibitors and decrease in pro-angiogenic factors, wherein inhibiting high-level expressions of pro-angiogenic factors, especially by targeting the VEGF/VEGFR signaling pathway, has become the mainstream objective of current studies.

VEGF is a glycoprotein in human bodies and plays an important role in angiogenesis. The human VEGF family includes VEGF-A, VEGF-B, VEGF-C, VEGF-D, VEGF-E, and PLGF. VEGF can selectively act on VEGFR (VEGF receptor) which is a class of tyrosine kinase trans-membrane proteins. Binding VEGF to VEGFR changes the conformation of VEGFR, and results in dimerization of the receptor and also phosphorylation of intracellular tyrosine sites, thereby activating downstream transduction pathways (Joukov, V., et. al. EMBO J., 1996, 15, 290-298). Extensive studies show that the VEGF/VEGFR signaling transduction pathway is the most important pro-angiogenic and migration pathway in cells. By inhibition of this pathway, growth and migration of endothelial cells can be inhibited, and in turn the growth of tumors can be inhibited. Currently, several such drugs have been approved and more than 30 drugs are in clinical trials. One important drug is a recombinant humanized VEGF monoclonal antibody called bevacizumab (trade name Avastin), which is the first approved drug against angiogenesis in tumors and is capable of specifically binding VEGF-A to block the VEGF/VEGFR pathway. This drug achieved great success initially after its approval, but the problem of drug resistance gradually emerged from its long-term use. Further studies reveal that specific inhibition of VEGF-A causes cells to release a large amount of other pro-angiogenic factors such as PLGF and FGF, and such a phenomenon is called angiogenesis rescue reaction. To solve the drug-resistance problem, one possible strategy is to develop multi-target inhibitors.

Sunitinib is just a multi-target anti-cancer drug developed by Pfizer, which is an inhibitor acting on multi-target tyrosine kinases and can effectively inhibit receptor tyrosine kinases such as VEGFR-1, VEGFR-2, VEGFR-3, PDGFR-13, and c-Kit, FLT-3. By inhibiting these proteins, sunitinib blocks expression of various pro-angiogenic factors in cancer cells, so that an objective to suppress neoangiogenesis and "starve" cancer cells to death can be realized (Abrams, T. J. et. al. Mol. Cancer Ther., 2003, 2, 1011-1021). Furthermore, sunitinib also shows direct specific inhibition against cancer cells having mutations in c-Kit and FLT-3. Sunitinib was approved by FDA in 2006, mainly for treatment of gastrointestinal stromal tumors and renal cell carcinoma, as the first anti-cancer drug approved for two kinds of indications at the same time. Although sunitinib shows remarkable anti-tumor efficacy, side effects such as lack of power, bone marrow depression and fever are still found in patients clinically administrated with sunitinib. Sunitinib shows strong accumulation in tissues and cannot be taken continuously, and in clinical scenarios its administration is performed successively for four weeks and is then stopped for two weeks. However, it is shown in research that neoangiogenesis in tumors recovers during the drug withdrawal. Therefore, it is necessary to modify the chemical structure to lower toxic side effects, optimize the druggability, and find safer and more efficacious medicaments.

SUMMARY OF INVENTION

An objective of the present invention is to provide a multi-target receptor tyrosine kinase inhibitor with high efficacy and low toxicity.

Another objective of the present invention is to provide a group of pyrrole-substituted indolone derivatives that inhibit tumor growth.

Yet another objective of the present invention is to provide a pharmaceutical composition comprising the pyrrole-substituted indolone derivatives.

Yet another objective of the present invention is to provide use of the pyrrole-substituted indolone derivatives and a pharmaceutical composition comprising the pyrrole-substituted indolone derivatives.

The present invention provides a pyrrole-substituted indolone derivative with a structure shown in general formula (I) below, or pharmaceutically acceptable salts thereof:

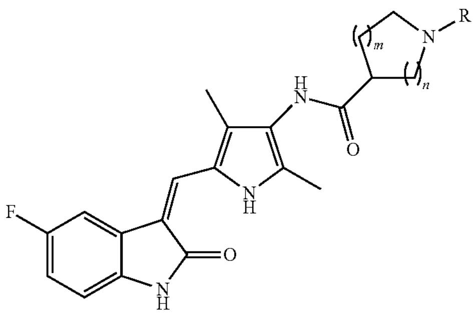

(I)

wherein m is selected from 0, 1 and 2;

n is selected from 1, 2 and 3; and

R is selected from hydrogen, a $C_1$-$C_6$ linear or branched alkyl, a $C_3$-$C_7$ cycloalkyl, formyl substituted with a $C_1$-$C_6$ linear or branched alkyl, $C_3$-$C_7$ cycloalkylformyl, t-butoxycarbonyl, substituted carbamoyl, or a 5- to 7-membered cyclic carbamoyl.

In the pyrrole-substituted indolone derivative above, R is preferably selected from hydrogen, a $C_1$-$C_3$ linear or branched alkyl, a $C_4$-$C_6$ cycloalkyl, formyl substituted with a $C_1$-$C_3$ linear or branched alkyl, $C_3$-$C_6$ cycloalkylformyl, t-butoxycarbonyl, N,N-dimethyl carbamoyl, N,N-diethyl carbamoyl, N,N-dipropyl carbamoyl, pyrrolidin-1-ylformyl, or piperidin-1-ylformyl.

In the pyrrole-substituted indolone derivative above, R is more preferably selected from hydrogen, methyl, t-butoxycarbonyl, N,N-dimethyl carbamoyl, or pyrrolidin-1-ylformyl.

According to the present invention, the pyrrole-substituted indolone derivative having a structure shown in the general formula (I) is preferably selected from Compounds 1 to 15 below:

| Compound No. | Structure of compound |
|---|---|
| 1 | 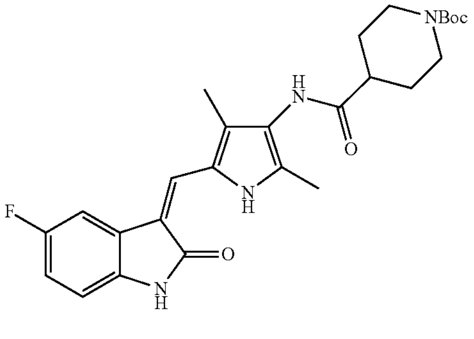 [SMILES: Cc1[nH]c(/C=C2\C(=O)Nc3ccc(F)cc32)c(C)c1NC(=O)C1CCN(C(=O)OC(C)(C)C)CC1] |
| 2 | 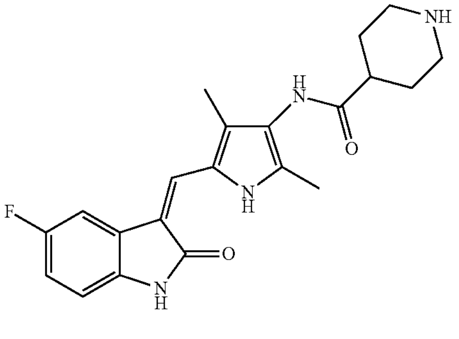 [SMILES: Cc1[nH]c(/C=C2\C(=O)Nc3ccc(F)cc32)c(C)c1NC(=O)C1CCNCC1] |

-continued
| Compound No. | Structure of compound |
| --- | --- |
| 3 | 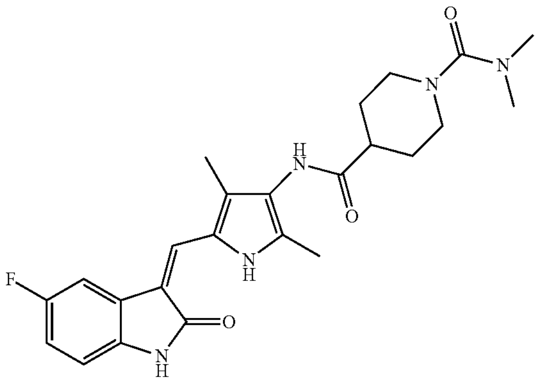 [SMILES: Cc1[nH]c(/C=C2\C(=O)Nc3ccc(F)cc32)c(C)c1NC(=O)C1CCN(C(=O)N(C)C)CC1] |
| 4 | 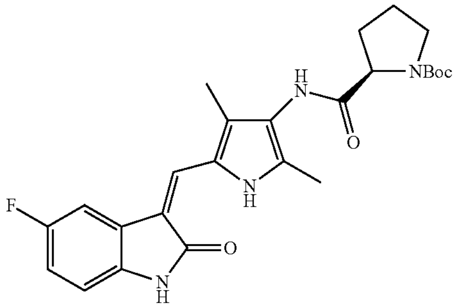 [SMILES: Cc1[nH]c(/C=C2\C(=O)Nc3ccc(F)cc32)c(C)c1NC(=O)[C@H]1CCCN1C(=O)OC(C)(C)C] |
| 5 | 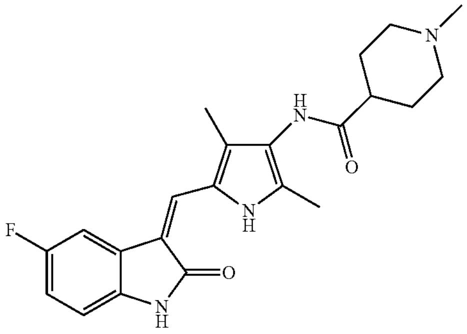 [SMILES: Cc1[nH]c(/C=C2\C(=O)Nc3ccc(F)cc32)c(C)c1NC(=O)C1CCN(C)CC1] |
| 6 | 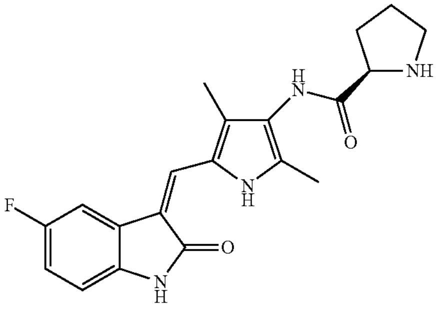 [SMILES: Cc1[nH]c(/C=C2\C(=O)Nc3ccc(F)cc32)c(C)c1NC(=O)[C@H]1CCCN1] |

-continued
| Compound No. | Structure of compound |
|---|---|
| 7 | 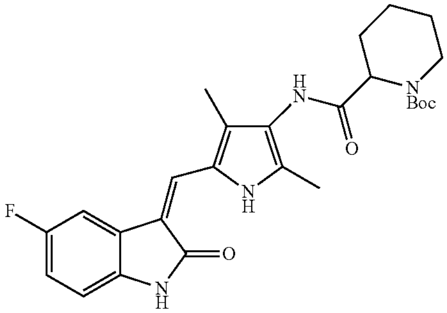 [SMILES: Cc1[nH]c(/C=C2\C(=O)Nc3ccc(F)cc32)c(C)c1NC(=O)C1CCCCN1C(=O)OC(C)(C)C] |
| 8 | 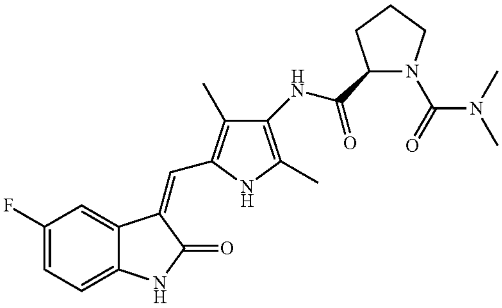 [SMILES: Cc1[nH]c(/C=C2\C(=O)Nc3ccc(F)cc32)c(C)c1NC(=O)[C@H]1CCCN1C(=O)N(C)C] |
| 9 | 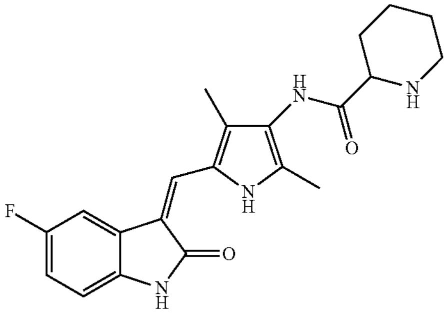 [SMILES: Cc1[nH]c(/C=C2\C(=O)Nc3ccc(F)cc32)c(C)c1NC(=O)C1CCCCN1] |
| 10 | 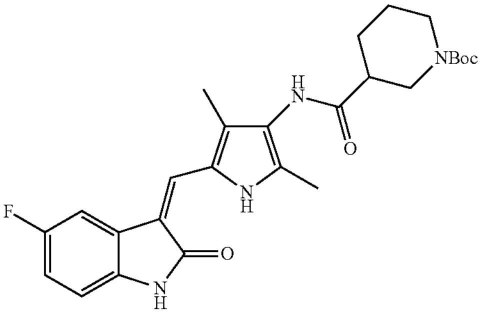 [SMILES: Cc1[nH]c(/C=C2\C(=O)Nc3ccc(F)cc32)c(C)c1NC(=O)C1CCCN(C(=O)OC(C)(C)C)C1] |

-continued
| Compound No. | Structure of compound |
|---|---|
| 11 | 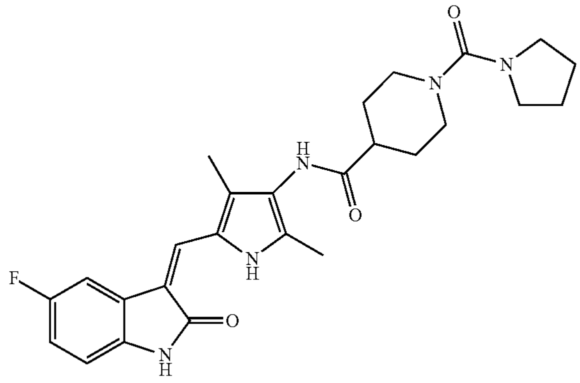 [SMILES: Cc1[nH]c(/C=C2\C(=O)Nc3ccc(F)cc32)c(C)c1NC(=O)C1CCN(C(=O)N2CCCC2)CC1] |
| 12 | 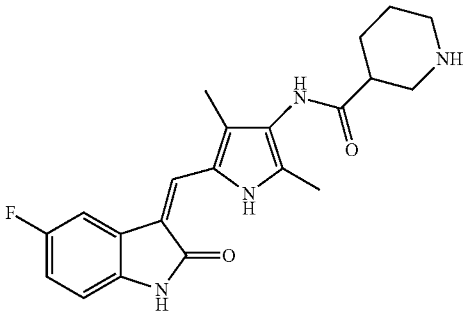 [SMILES: Cc1[nH]c(/C=C2\C(=O)Nc3ccc(F)cc32)c(C)c1NC(=O)C1CCCNC1] |
| 13 | 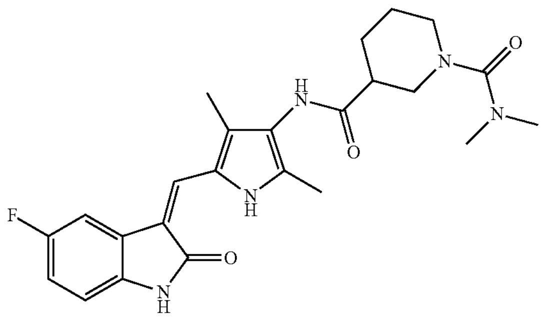 [SMILES: Cc1[nH]c(/C=C2\C(=O)Nc3ccc(F)cc32)c(C)c1NC(=O)C1CCCN(C(=O)N(C)C)C1] |
| 14 | 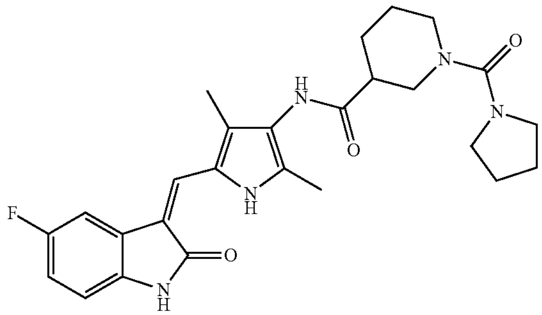 [SMILES: Cc1[nH]c(/C=C2\C(=O)Nc3ccc(F)cc32)c(C)c1NC(=O)C1CCCN(C(=O)N2CCCC2)C1] |

-continued

| Compound No. | Structure of compound |
| --- | --- |
| 15 | 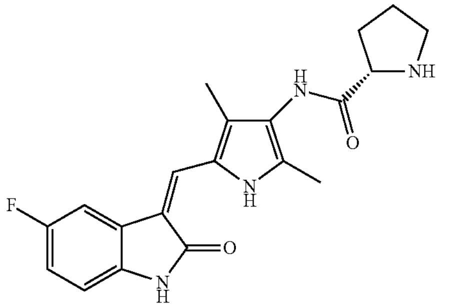 [SMILES: Cc1[nH]c(/C=C2\C(=O)Nc3ccc(F)cc32)c(C)c1NC(=O)[C@@H]1CCCN1] |

The pharmaceutically acceptable salts of the pyrrole-substituted indolone derivative according to the present invention are not particularly limited, and may be hydrochloride, fumarate, maleate, citrate, phosphate, sulfate, tartrate, methanesulfonate, benzenesulfonate, etc. Use of hydrochloride may bring about high crystallinity and high solubility, and improve hygroscopicity. Therefore, use of hydrochloride is preferred.

In the second aspect of the present invention, there provided a method for preparing the pyrrole-substituted indolone derivative according to the present invention, comprising the steps of:

(a) nitrating 3,5-dimethyl-2-pyrrolealdehyde shown in structural formula I with $KNO_3$ in concentrated sulfuric acid, to produce a compound shown in structural formula II:

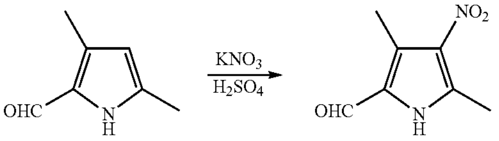

I II

Specifically, dissolving 3,5-dimethyl-2-pyrrolealdehyde shown in structural formula I in concentrated sulfuric acid, lowering the temperature to around −10° C., then adding $KNO_3$, and allowing the reaction to proceed while maintaining the temperature; after the reaction is completed, adding into cold water, followed by vigorously stirring and filtration, to obtain the compound II, which is then recrystallized to produce a pure product;

(b) condensing 3,5-dimethyl-4-nitro-2-pyrrolealdehyde shown in structural formula II with 5-fluoroindolone shown in formula structural III under the catalysis of pyrrolidine, to produce a compound shown in structural formula IV:

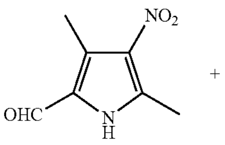

II

-continued

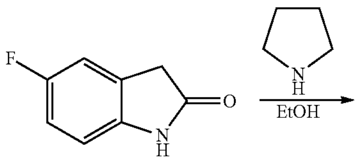

III

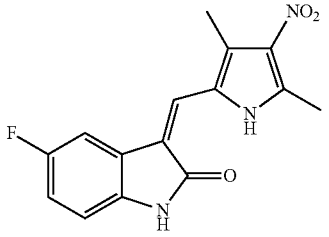

IV

Specifically, adding 3,5-dimethyl-4-nitro-2-pyrrolealdehyde shown in structural formula II to ethanol, elevating the temperature to 50° C., then adding 5-fluoroindolone shown in structural formula III, and allowing the reaction to proceed while maintaining the temperature; after the reaction is completed, performing filtration to obtain a pure product of the compound IV;

(c) reducing the compound shown in structural formula IV with zinc powder to produce a compound shown in structural formula V:

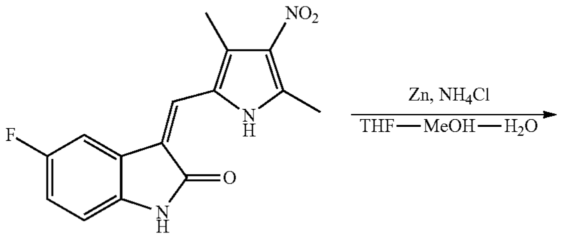

IV

-continued

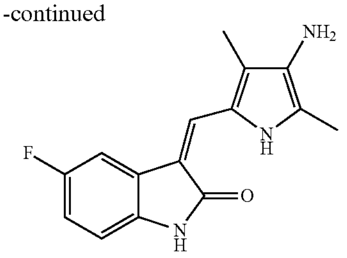

V

Specifically, dissolving the compound shown in structural formula IV in a mixed solution of tetrahydrofuran, water and methanol, elevating the temperature to 50° C., adding saturated ammonium chloride and zinc powder, and allowing the reaction to proceed while maintaining the temperature; after the reaction is completed, evaporating off the solvent, and performing extraction with ethyl acetate to obtain a pure product of the compound V;

(d) condensing the compound shown in structural formula V with a corresponding acid VI to produce a compound shown in structural formula VII:

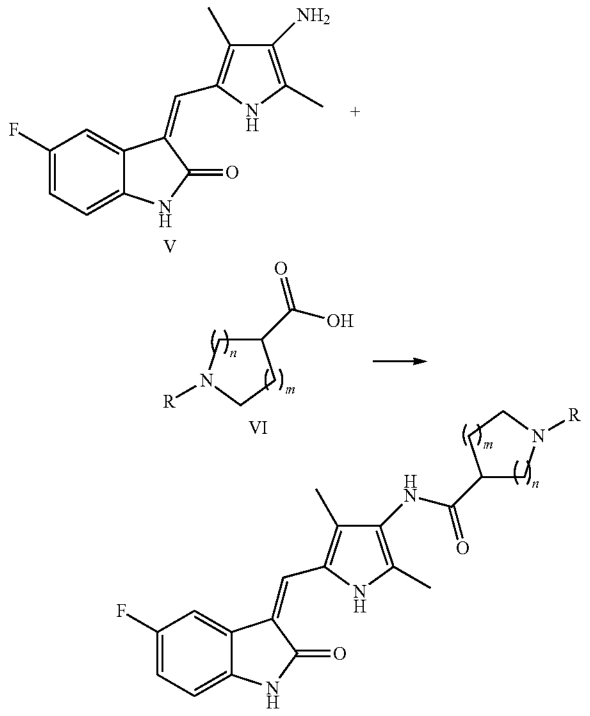

V VI VII

Specifically, dissolving the compound shown in structural formula V in tetrahydrofuran, adding an alkali (DIPEA, DMAP, pyridine or the like) and a condensing agent (EDCI, DCC or the like) thereto at room temperature, and allowing the reaction to proceed while maintaining the temperature; after the reaction is completed, evaporating off the solvent to obtain a crude product of the compound shown in structural formula VII, washing it with water, followed by rinsing with a solvent (ethyl acetate, methanol or the like), to obtain a pure product of the compound VII.

According to the present invention, there provided a pharmaceutical composition comprising a therapeutically effective amount of one or more pyrrole-substituted indolone derivatives shown in general formula (I) or pharmaceutically acceptable salts thereof, and the composition may further comprise pharmaceutically conventional auxiliaries such as excipient, sweeteners, and the like.

The pyrrole-substituted indolone derivatives or pharmaceutically acceptable salts thereof according to the present invention have activity of inhibiting tyrosine kinases, and can be used in the manufacture of a medicament for treating tumors caused by abnormal expression of tyrosine kinases. That is, the pyrrole-substituted indolone derivatives or pharmaceutically acceptable salts thereof according to the present invention can be used to treat tyrosine kinase-mediated tumors and inhibit cell growth of relevant tumors, which includes administrating a therapeutically effective amount of the pyrrole-substituted indolone derivatives or pharmaceutically acceptable salts thereof to a patient. The pyrrole-substituted indolone derivatives or pharmaceutically acceptable salts thereof can also be used to manufacture a medicament for treating tyrosine kinase-mediated tumors and inhibiting cell growth of relevant tumors.

Beneficial Effects

The pyrrole-substituted indolone derivatives or pharmaceutically acceptable salts thereof prepared according to the present invention exhibit inhibition of many tyrosine kinases, and can inhibit tumor growth as generally demonstrated in animal experiments. Particularly, the pyrrole-substituted indolone derivatives or pharmaceutically acceptable salts thereof according to the present invention have a very low level of toxic side effects. These compounds can be used to treat many tumor diseases. The compounds according to the invention are simple to synthesize, easy to prepare, and can be synthesized from widely available raw materials.

DETAILED DESCRIPTION OF INVENTION

The present invention will be further described below in conjunction with specific examples, but is not limited thereto.

In the preparation examples below, $^1$H-NMR was measured with Varian Mercury AMX300, 400, 500 apparatus; MS was measured with VG ZAB-HS or VG-7070 and Esquire 3000 plus-01005; all solvents were redistilled before use; all anhydrous solvents used were obtained by drying according to standard methods; unless otherwise indicated, all reactions were conducted under the protection of argon and traced with TLC; post treatments were all performed through washing with a saturated NaCl solution and drying with anhydrous $MgSO_4$; unless otherwise indicated, products were purified by silica gel column chromatography where the silica gel is 200- to 300-mesh $GF_{254}$ manufactured by Qingdao Haiyang Chemical Co., Ltd. or Yantai Yuanbo Silica Gel Company.

PREPARATION EXAMPLE 1

Preparation of Compound 1

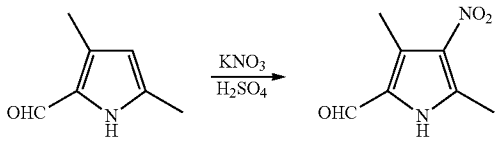

I II 3,5-dimethyl-2-pyrrolealdehyde I as a raw material (5 g, 40 mmol) was dissolved in 60 mL concentrated sulfuric acid, then the temperature of the system was lowered to −10° C., at which temperature $KNO_3$ (4.35 g, 42 mmol) was slowly added in batches over about 2 h, during which the temperature was maintained at −10° C., and the solution was further stirred for about 2 h at this temperature after the addition of $KNO_3$ was completed. Upon completion of the reaction as indicated by TLC, the resultant solution was added to 1 μL ice water, and extracted twice with a total of 1 L ethyl acetate. The organic layer was washed with a saturated NaCl solution, dried over anhydrous sodium sulfate, and filtered. Then the organic solvents were evaporated off at reduced pressure to obtain 7 g crude product, which was added to 10-20 mL ethyl acetate, followed by vigorous stirring, to obtain 5 g pure product of the target compound II.

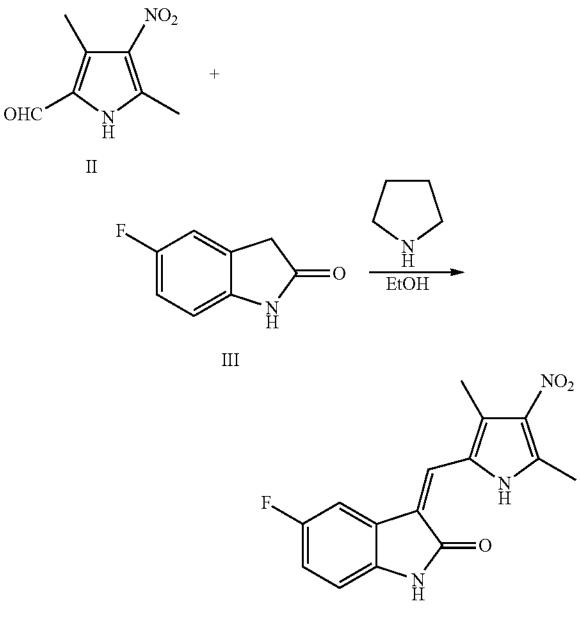

II

III

IV

Compound II (1.68 g, 10 mmol) and Compound III (1.8 g, 12 mmol) were added to 50 mL anhydrous ethanol, and tetrahydropyrrole (850 mg, 12 mmol) was added thereto at room temperature. The system turned yellow after the addition. The temperature was elevated to 50° C., and the reaction was allowed to proceed for 2 h at this temperature. After the reaction was completed, the system was directly filtered, and the filter cake was washed with a small volume of ethanol and ethyl acetate, to obtain 2.7 g pure product of the target compound IV. $^1$H NMR (400 MHz, DMSO-$d_6$) δ 11.14 (s, 1H), 7.88 (dd, J=9.2, 2.4 Hz, 1H), 7.82 (s, 1H), 7.05-6.97 (m, 1H), 6.88 (dd, J=8.5, 4.5 Hz, 1H), 2.64 (s, 3H), 2.58 (s, 3H).

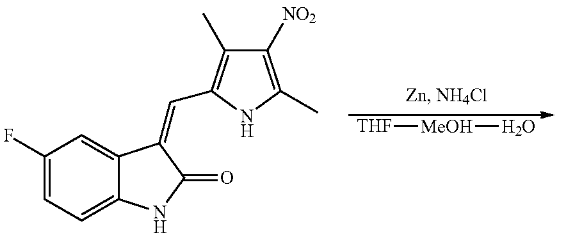

IV

-continued

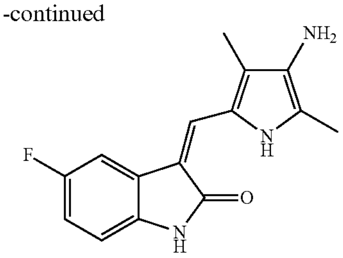

V

Compound IV (900 mg, 3 mmol) was placed in a 500-mL two-necked flask, and then 200 mL of tetrahydrofuran, 100 mL of methanol, 60 mL of water and a 60 mL of saturated ammonium chloride solution were respectively added thereto. Then the temperature was elevated to 50° C., and zinc powder (1.8 g, 30 mmol) was added under stirring, followed by 2 h reaction at this condition, during which the system turned clear first and then turbid. After the system turned turbid, completion of the reaction was indicated by LC-MS. After completion of the reaction, the solvent was evaporated off. The system was adjusted to be alkaline with a saturated sodium carbonate solution, and extracted twice with a total of 2 μL of ethyl acetate. The ethyl acetate layer was washed with a saturated NaCl solution, dried over anhydrous sodium sulfate, and filtered. Then the organic solvents were evaporated off at reduced pressure to obtain the target compound V (800 mg).

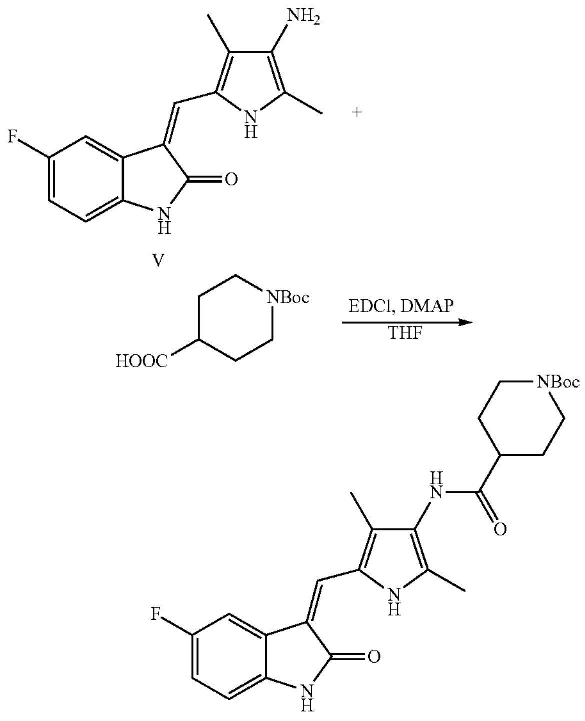

V

1

Compound V (270 mg, 1 mmol) was dissolved in tetrahydrofuran (20 mL), and Boc-protected 4-piperidinecarboxylic acid (270 mg, 1.2 mmol), EDCI (220 mg, 1.1 mmol), DIPEA (260 mg, 2 mmol) and a catalytic amount of DMAP were added thereto at room temperature. After the addition, the reaction was allowed to proceed at room temperature for about 8 h, and its completion was indicated by TLC. After the reaction was completed, the tetrahydrofuran solution was evaporated off, and a large volume of ethyl acetate and water were added for partitioning, followed by filtration to obtain a crude product of the target compound. The crude product was rinsed with methanol to obtain a pure product of Compound 1. $^{1}$H NMR (400 MHz, DMSO-$d_6$) δ 13.59 (s, 1H), 10.83 (s, 1H), 9.12 (s, 1H), 7.71 (dd, J=9.5, 2.6 Hz, 1H), 7.66 (s, 1H), 6.93-6.86 (m, 1H), 6.86-6.81 (m, 1H), 3.99-3.95 (m, 2H), 3.10-2.94 (m, 1H), 2.79-2.75 (m, 2H), 2.17 (s, 3H), 2.15 (s, 3H), 1.82-1.78 (m, 2H), 1.55-1.45 (m, 2H), 1.41 (s, 9H).

PREPARATION EXAMPLE 2

Preparation of Compound 2

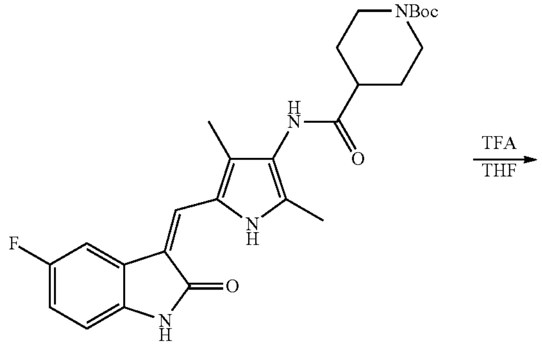

1

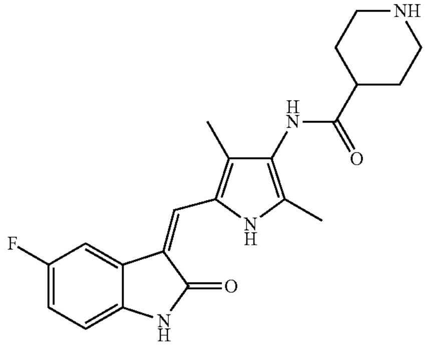

2

Compound 1 (480 mg, 1 mmol) was added to 10 ml tetrahydrofuran, and 10 mL trifluoroacetic acid was added thereto at room temperature. Then the temperature was elevated to 50° C. and the reaction was allowed to proceed for about 2 h, of which completion was indicated by LC-MS. After the reaction was completed, most of the solution was evaporated off, and the rest was neutralized with a saturated sodium carbonate solution, followed by filtration to obtain a crude product. The crude product was rinsed with ethyl acetate and methanol to obtain a pure product of Compound 2. $^{1}$H NMR (400 MHz, DMSO-$d_6$) δ 13.60 (s, 1H), 10.85 (s, 1H), 9.26 (s, 1H), 7.71 (dd, J=9.5, 2.4 Hz, 1H), 7.67 (s, 1H), 6.94-6.86 (m, 1H), 6.87-6.83 (m, 1H), 3.34 (d, J=12.3 Hz, 2H), 3.06-2.89 (m, 2H), 2.74-2.59 (m, 1H), 2.18 (s, 3H), 2.16 (s, 3H), 2.05-1.94 (m, 2H), 1.89-1.74 (m, 2H).

PREPARATION EXAMPLE 3

Preparation of Compound 3

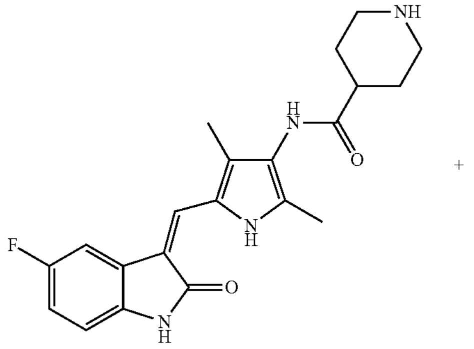

+

2

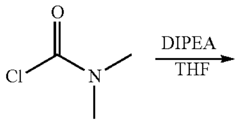

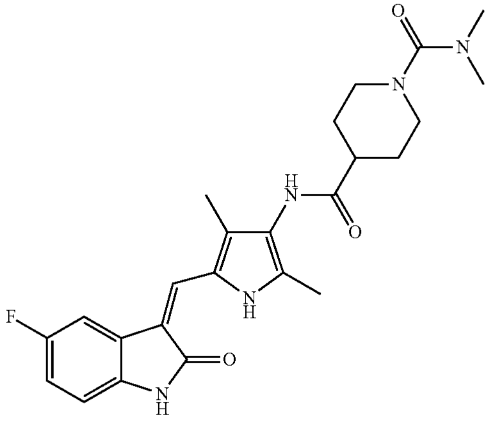

3

Compound 2 (383 mg, 1 mmol) was added to 20 mL of tetrahydrofuran, and DIPEA (260 mg, 2 mmol) and dimethylcarbamoyl chloride (214 mg, 2 mmol) were added thereto at room temperature. Then the reaction was allowed to proceed for about 12 h, and was nearly completed as indicated by TLC. After the reaction was completed, the solvents were evaporated off, and the solid was rinsed with 20 mL of ethyl acetate and 10 mL of methanol, to obtain a pure product of the target compound 3. $^{1}$H NMR (400 MHz, DMSO-$d_6$) δ 13.58 (s, 1H), 10.82 (s, 1H), 9.10 (s, 1H), 7.70 (dd, J=9.5, 2.5 Hz, 1H), 7.66 (s, 1H), 6.95-6.86 (m, 1H), 6.85-6.77 (m, 1H), 3.87-3.70 (m, 1H), 3.63-3.54 (m, 2H), 2.86-2.58 (m, 8H), 2.18 (s, 3H), 2.15 (s, 3H), 1.85-1.76 (m, 2H), 1.71-1.55 (m, 2H).

PREPARATION EXAMPLE 4

Preparation of Compound 4

4

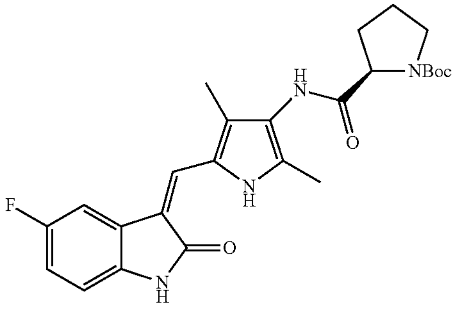

The protocol was the same as the synthesis method 1 above, except that Boc-protected proline was used instead of Boc-protected piperidinecarboxylic acid to obtain the target compound 4. $^{1}$H NMR (400 MHz, DMSO) δ 13.59 (s, 0.6H), 13.58 (s, 0.4H), 10.84 (s, 1H), 9.20 (s, 0.6H), 9.13 (s, 0.4H), 7.70 (dd, J=9.5, 2.5 Hz, 1H), 7.66 (d, J=3.0 Hz, 1H), 6.89 (dd, J=12.5, 5.5 Hz, 1H), 6.83 (dd, J=8.4, 4.7 Hz, 1H), 4.38-4.15 (m, 1H), 3.52-3.41 (m, 1H), 3.35-3.28 (m, 1H), 2.35-2.22 (m, 1H), 2.21 (s, 2H), 2.18 (s, 3H), 2.16 (s, 1H), 1.98-1.79 (m, 3H), 1.43 (s, 3H), 1.39 (s, 6H) (the Boc substituent cannot rotate freely to produce an isomer).

PREPARATION EXAMPLE 5

Preparation of Compound 5

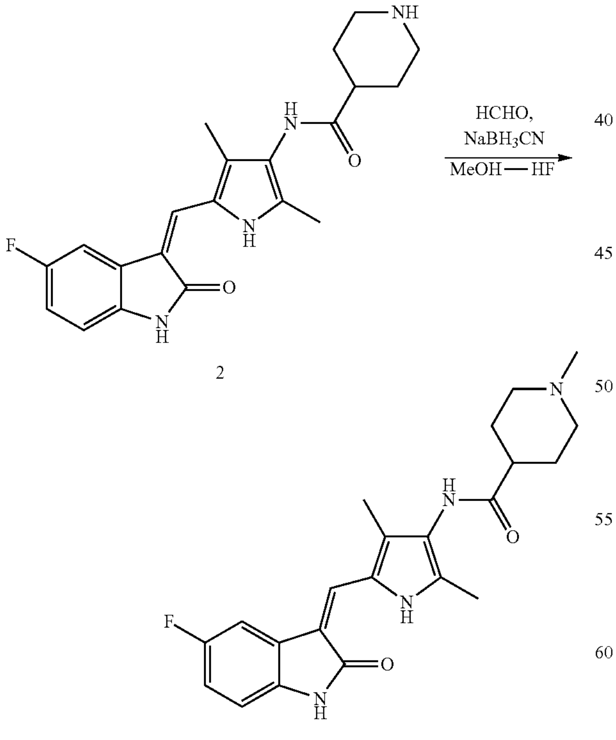

2

5

Compound 2 (383 mg, 1 mmol) was added to a 20 ml mixed (1:1) solvent of tetrahydrofuran and methanol, and an aqueous solution of formaldehyde (500 mg, 5 mmol) and sodium cyanoborohydride (120 mg, 2 mmol) were added thereto at room temperature. After the addition, the reaction was allowed to proceed for 12 h, and its process was monitored by TLC. After the reaction was completed, the solvents were evaporated off, and the target compound 5 was obtained by column chromatography. $^{1}$H NMR (400 MHz, DMSO-$d_6$) δ 13.58 (s, 1H), 10.83 (s, 1H), 9.05 (s, 1H), 7.70 (dd, J=9.5, 2.4 Hz, 1H), 7.66 (s, 1H), 6.93-6.86 (m, 1H), 6.85-6.80 (m, 1H), 2.87-2.77 (m, 2H), 2.36-2.21 (m, 1H), 2.17 (s, 3H), 2.16 (s, 3H), 2.15 (s, 3H), 1.94-1.59 (m, 6H).

PREPARATION EXAMPLE 6

Preparation of Compound 6

6

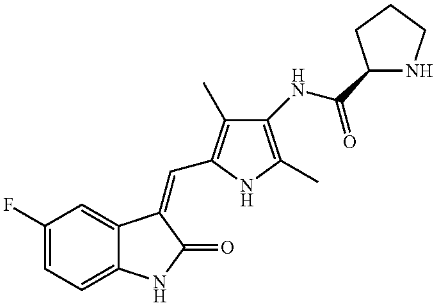

The synthesis of compound 6 was the same as that for compound 2, except that compound 4 was used instead of compound 1 to obtain the target compound 6. $^{1}$H NMR (400 MHz, DMSO-$d_6$) δ 13.60 (s, 1H), 10.83 (s, 1H), 9.23 (s, 1H), 7.71 (dd, J=9.3, 2.4 Hz, 1H), 7.67 (s, 1H), 6.93-6.87 (m, 1H), 6.83 (dd, J=8.4, 4.6 Hz, 1H), 3.70 (dd, J=8.7, 5.5 Hz, 1H), 2.91 (t, J=6.6 Hz, 1H), 2.18 (s, 2H), 2.16 (s, 2H), 2.10-1.98 (m, 1H), 1.85-1.74 (m, 1H), 1.72-1.63 (m, 2H).

PREPARATION EXAMPLE 7

Preparation of Compound 7

7

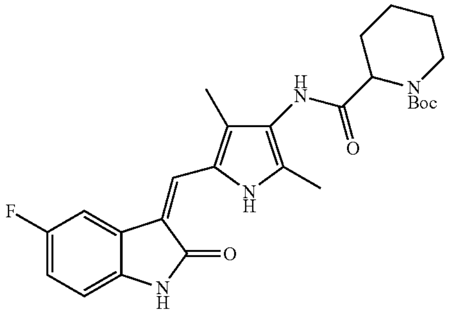

The synthesis of compound 7 was the same as that for compound 1, except that Boc-protected 2-piperidinecarboxylic acid was used instead of Boc-protected 4-piperidinecarboxylic acid to obtain the target compound 7. $^{1}$H NMR (400 MHz, DMSO-$d_6$) δ 13.60 (s, 1H), 10.84 (s, 1H), 9.16 (s, 1H), 7.71 (dd, J=9.5, 2.5 Hz, 1H), 7.67 (s, 1H), 6.94-6.87 (m, 1H), 6.85-6.81 (m, 1H), 4.79-4.63 (m, 1H), 3.87-3.75 (m, 1H), 3.30-3.09 (m, 1H), 2.19 (s, 3H), 2.17 (s, 3H), 1.81-1.59 (m, 3H), 1.41 (s, 9H), 1.44-1.22 (m, 3H).

PREPARATION EXAMPLE 8

Preparation of Compound 8

8

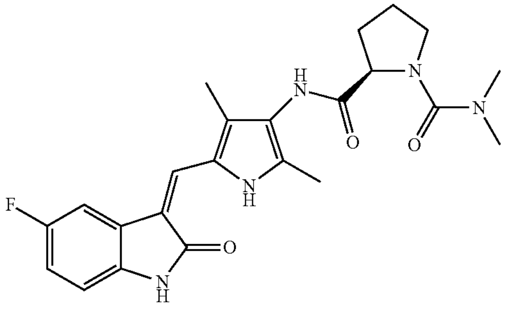

The synthesis of compound 8 was the same as that for compound 3, except that compound 4 was used instead of compound 2 to obtain the target compound 8. $^1$H NMR (400 MHz, DMSO-$d_6$) δ 13.59 (s, 1H), 10.84 (s, 1H), 8.99 (s, 2H), 7.74-7.68 (m, 1H), 7.66 (s, 1H), 6.93-6.86 (m, 1H), 6.83 (dd, J=8.4, 4.6 Hz, 1H), 4.39 (t, J=7.4 Hz, 1H), 3.60-3.44 (m, 1H), 3.43-3.37 (m, 1H), 2.80 (s, 6H), 2.28-2.20 (m, 1H), 2.16 (s, 3H), 2.14 (s, 3H), 1.97-1.88 (m, 1H), 1.87-1.70 (m, 2H).

PREPARATION EXAMPLE 9

Preparation of Compound 9

9

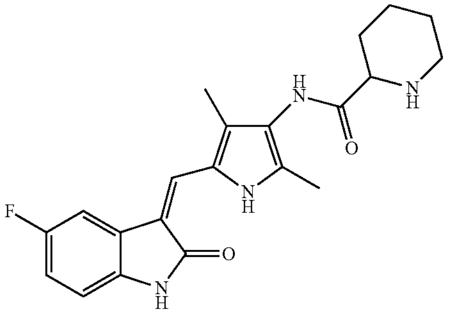

The synthesis of compound 8 was the same as that for compound 3, except that compound 4 was used instead of compound 2 to obtain the target compound 9. $^1$H NMR (400 MHz, DMSO-$d_6$) δ 13.59 (s, 1H), 10.83 (s, 1H), 8.97 (s, 1H), 7.70 (dd, J=9.6, 2.5 Hz, 1H), 7.66 (s, 1H), 6.92-6.86 (m, 1H), 6.84-6.81 (m, 1H), 3.30-3.25 (m, 1H), 2.99 (d, J=13.2 Hz, 1H), 2.60 (t, J=11.3 Hz, 1H), 2.18 (s, 2H), 2.16 (s, 2H), 1.91-1.73 (m, 2H), 1.56-1.33 (m, 4H).

PREPARATION EXAMPLE 10

Preparation of Compound 10

10

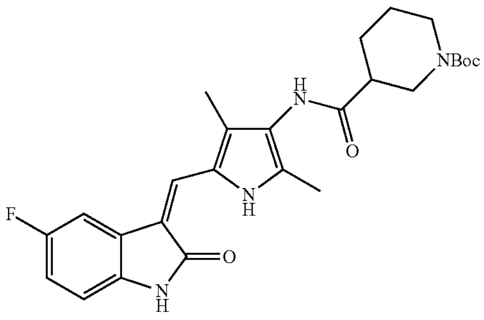

The synthesis of compound 10 was the same as that for compound 3, except that compound 4 was used instead of compound 2 to obtain the target compound 10. $^1$H NMR (400 MHz, DMSO-$d_6$) δ 13.59 (s, 1H), 10.83 (s, 1H), 9.20 (s, 1H), 7.71 (dd, J=9.4, 2.5 Hz, 1H), 7.67 (s, 1H), 6.89 (dd, J=13.8, 6.7 Hz, 1H), 6.86-6.82 (m, 1H), 4.13-4.02 (m, 1H), 3.89 (d, J=13.1 Hz, 1H), 2.94-2.72 (m, 2H), 2.48-2.41 (m, 1H), 2.18 (s, 3H), 2.16 (s, 3H), 2.01-1.94 (m, 1H), 1.73-1.57 (m, 2H), 1.42 (s, 9H), 1.39-1.24 (m, 1H).

PREPARATION EXAMPLE 11

Preparation of Compound 11

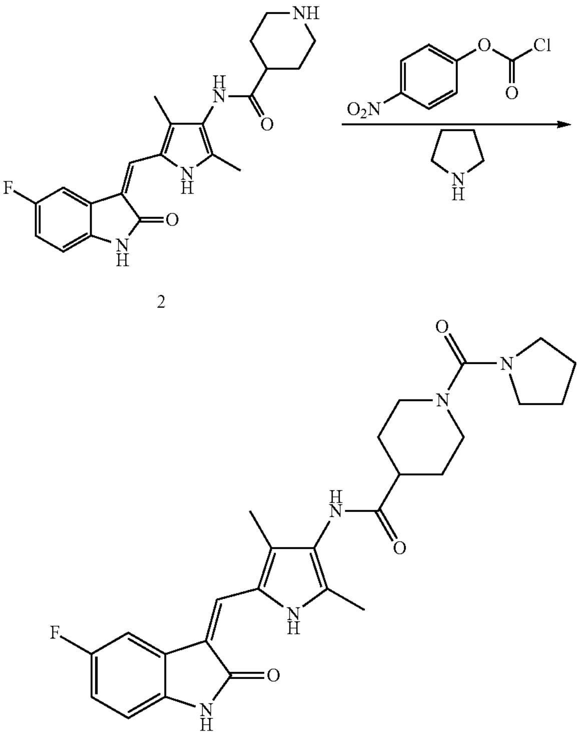

2

11

Compound 2 (383 mg, 1 mmol) was added to 20 mL of tetrahydrofuran, and DIPEA (260 mg, 2 mmol) and p-nitrophenyl chloroformate (240 mg, 1.2 mmol) were added thereto at room temperature. After the addition, the reaction was allowed to proceed for about 12 h, and was nearly completed as indicated by TLC. After the reaction was completed, tetrahydropyrrole (142 mg, 2 mmol) and an excess amount of DIPEA (260 mg, 2 mmol) were added, followed by further reaction for not less than 12 h, which was monitored by TLC. After the reaction was completed, the solvents were evaporated off, and the solid was rinsed with 20 mL of ethyl acetate and 10 mL of methanol, to obtain a pure product of the target compound 11. $^1$H NMR (400 MHz, DMSO-$d_6$) δ 13.58 (s, 1H), 10.82 (s, 1H), 9.09 (s, 1H), 7.70 (dd, J=9.4, 2.5 Hz, 1H), 7.66 (s, 1H), 6.93-6.86 (m, 1H), 6.83 (dd, J=8.5, 4.6 Hz, 1H), 3.70 (d, J=13.5 Hz, 2H), 3.27 (t, J=6.4 Hz, 4H), 2.73 (t, J=11.6 Hz, 1H), 2.18 (s, 3H), 2.15 (s, 3H), 1.86-1.71 (m, 6H), 1.67-1.54 (m, 2H).

PREPARATION EXAMPLE 12

Preparation of Compound 12

12

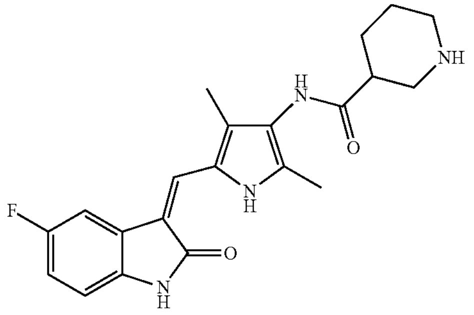

The synthesis of compound 12 was the same as that for compound 2, except that compound 10 was used instead of compound 1 to obtain the target compound 12. $^1$H NMR (400 MHz, DMSO-$d_6$) δ 13.59 (s, 1H), 10.90 (s, 1H), 9.17 (s, OH), 7.69 (dd, J=9.4, 2.4 Hz, 1H), 7.65 (s, 1H), 6.94-6.82 (m, 2H), 3.67-3.52 (m, 2H), 3.15-2.56 (m, 3H), 2.45 (d, J=10.0 Hz, 2H), 2.17 (s, 3H), 2.15 (s, 3H), 1.89 (d, J=9.2 Hz, 1H), 1.61 (d, J=10.4 Hz, 2H), 1.42 (s, 1H).

PREPARATION EXAMPLE 13

Preparation of Compound 13

13

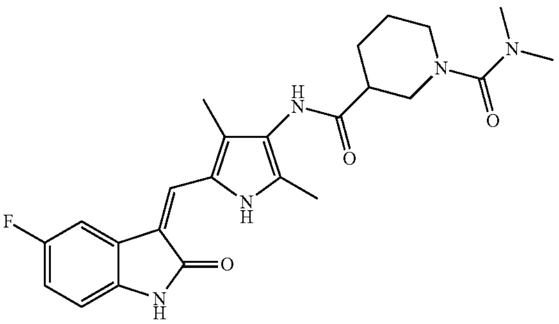

The synthesis of compound 13 was the same as that for compound 3, except that compound 12 was used instead of compound 2 to obtain the target compound 13. $^1$H NMR (400 MHz, DMSO-$d_6$) δ 13.59 (s, 1H), 10.83 (s, 1H), 9.18 (s, 1H), 7.71 (dd, J=9.4, 2.4 Hz, 1H), 7.66 (s, 1H), 6.89 (dd, J=9.2, 2.4 Hz, 1H), 6.86-6.80 (m, 1H), 3.72-3.59 (m, 1H), 3.51 (d, J=13.2 Hz, 1H), 2.90-2.81 (m, 1H), 2.78-2.68 (m, 7H), 2.64-2.55 (m, 1H), 2.18 (s, 3H), 2.15 (s, 3H), 1.97 (d, J=14.9 Hz, 1H), 1.73-1.57 (m, 2H), 1.53-1.38 (m, 1H).

PREPARATION EXAMPLE 14

Preparation of Compound 14

14

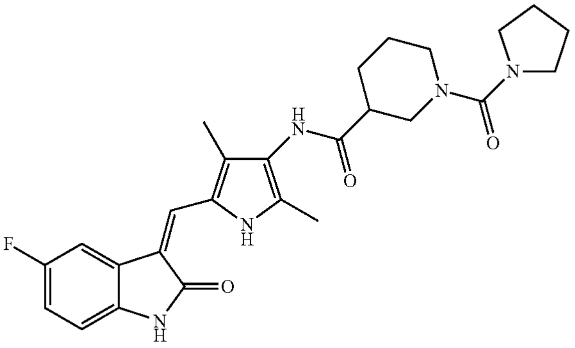

The synthesis of compound 14 was the same as that for compound 11, except that compound 12 was used instead of compound 2, to obtain the target compound 14. $^1$H NMR (400 MHz, DMSO-$d_6$) δ 13.59 (s, 1H), 10.83 (s, 1H), 9.18 (s, 1H), 7.71 (dd, J=9.4, 2.5 Hz, 1H), 7.66 (s, 1H), 6.93-6.86 (m, 1H), 6.83 (dd, J=8.4, 4.8 Hz, 1H), 3.75 (d, J=12.7 Hz, 1H), 3.61 (d, J=12.4 Hz, 1H), 3.28 (s, 4H), 2.90-2.81 (m, 1H), 2.73 (t, J=11.4 Hz, 1H), 2.60-2.50 (m, 1H), 2.06-1.91 (m, 1H), 1.76 (s, 4H), 1.74-1.59 (m, 2H), 1.55-1.39 (m, 1H).

PREPARATION EXAMPLE 15

Preparation of Compound 15

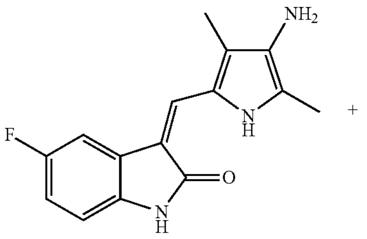

5

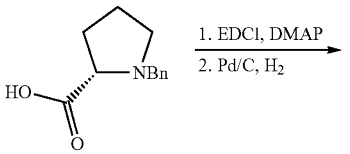

-continued

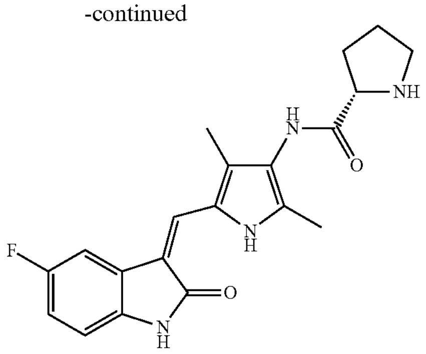

15

The synthesis in this procedure was the same as that for compound 6, except that D-N-Bn proline was used instead of the L-N-Bn proline to obtain the target compound. $^1$H NMR (400 MHz, DMSO) δ 13.60 (s, 1H), 10.83 (s, 1H), 9.23 (s, 1H), 7.71 (dd, J=9.3, 2.4 Hz, 1H), 7.67 (s, 1H), 6.93-6.87 (m, 1H), 6.83 (dd, J=8.4, 4.6 Hz, 1H), 3.70 (dd, J=8.7, 5.5 Hz, 1H), 2.91 (t, J=6.6 Hz, 1H), 2.18 (s, 2H), 2.16 (s, 2H), 2.10-1.98 (m, 1H), 1.85-1.74 (m, 1H), 1.72-1.63 (m, 2H).

PREPARATION EXAMPLE 16

Preparation of Hydrochloride of Compound 6

A 0.5 mL of saturated solution of HCl in ethanol was diluted 10 folds with anhydrous ethanol, and Compound 6 (368 mg, 1 mmol) was added thereto, followed by stirring for 5 to 10 min. The reaction solution was concentrated at reduced pressure, washed with a small volume of methanol, and hydrochloride of Compound 6 was then obtained.

The hydrochlorides of all the other compounds can be prepared by the above method, in which the corresponding compound reacts with a dilute solution of HCl in ethanol.

With reference to the above preparation examples for pyrrole-substituted indolone derivatives, other derivatives of this kind can also be prepared by the above method.

The applicant also synthesized the following Comparative compounds 1-3 by methods similar to the above or by other methods well known in the art.

Comparative compound 1

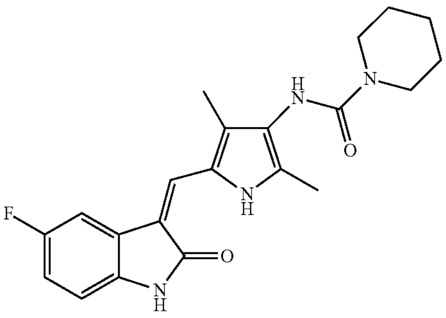

Comparative compound 1 is the same as Compound 2 except that the piperidinyl on the far right side is attached to the carbonyl via its N atom.

Comparative compound 2

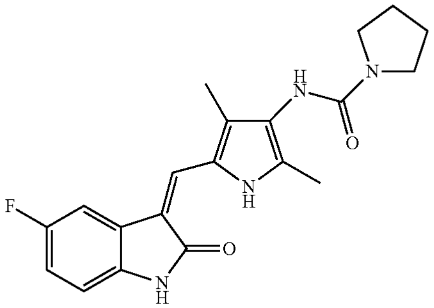

Comparative compound 2 is the same as Compound 6 except that the pyrrolidinyl on the far right side is attached to the carbonyl via its N atom.

Comparative compound 3

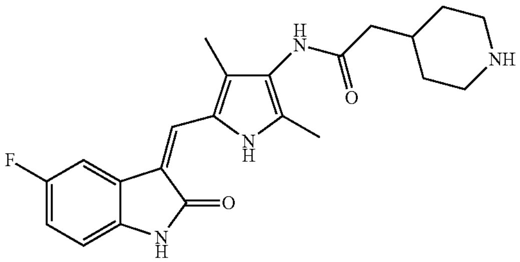

Comparative compound 3 is the same as Compound 2 except that the piperidinyl on the far right side is attached to the carbonyl via a methylene group.

EXAMPLES

The present invention will be further described below in conjunction with specific examples, but these examples are not to be construed as limiting the present invention.

Experimental Example 1

In Vitro Assay of Biochemical Activity on KDR Tyrosine Kinase

In vitro inhibitory activity of the compounds on KDR (VEGF receptor) tyrosine kinase was assayed by the HTRF (homogeneous time-resolved fluorescence) method. A mixture of a kinase buffer, the test compound or sunitinib, the substrate and an ATP solution was added to a final volume of 10 μL in a 384-well plate, which was incubated at room temperature for an appropriate period. 10 μl SA-XL665 and a TK antibody were added to each well, which was incubated at room temperature for 1 h and read with Synergy2.

The results showed that all the compounds in the above examples had significant inhibitory activity on KDR at the concentrations of 0.1 M and 1 M, and Compounds 3, 6, 8, 9, 11 and 13 were similar to sunitinib in activity.

TABLE 1

| In vitro inhibitory activity of example compounds on KDR | |
|---|---|
| | $IC_{50}$ (nM) |
| 2 | 290 |
| 3 | 78 |
| 5 | 141 |
| 6 | 83 |
| 8 | 66 |
| 9 | 89 |
| 11 | 74 |
| 12 | 142 |
| 13 | 77 |
| 14 | 143 |
| 15 | 65 |
| Sunitinib | 62 |
| Staurosporine* | 8.14 |

*Staurosporine was used as a positive control.

Experimental Example 2

Assays for Cytotoxicity to HUVEC and Activity on VEGF-Induced In Vitro Proliferation of HUVEC Cells Assays for inhibitory activity on VEGF-induced proliferation of Human umbilical veins epithelial cell (HUVEC) line: HUVECs were cultured in F-12K containing 10% FBS, 18 u/mL heparin and 30 g/mL ECGS, and HUVECs at 4-8 passages were selected for the experiment. The cells were digested with pancreatin, re-suspended in culture media ($1\times10^5$/mL), and were added to a 96-well plate with 100 μL/well, for overnight adherent culturing. The culture was replaced with an F-12K culture solution containing 5% FBS and the cells were cultured for 24 h. A 5% FBS F-12K culture solution containing the test compound, sunitinib, or a control was added and incubated for 30 min. A 0.1% FBS F-12K culture solution containing VEGF165 at a final concentration of 30 ng/ml or the vehicle (DMSO) was added and the cells were cultured under induction for 72 h. The culture solution was removed by pipetting, and 120 μL MTS assay solution was added to each well, which was incubated at 37° C. The $OD_{490}$ was read. The group treated with a 5% FBS F-12K culture solution served as the negative control. VEGF-stimulated growth value was obtained by subtracting the OD of the negative control group from the OD of the VEGF165-stimulated group, and used for calculation of inhibition. A dose-effect curve was drawn using the GraphPad Prism software, and half effective concentration ($EC_{50}$) was calculated.

Assays for cytotoxicity: the above HUVECs were cultured in an F-12K culture medium containing 10% fetal bovine serum (FBS), 100 U/mL penicillin, 100 g/mL streptomycin, 30 ug/mL ECGS, and 18 u/mL heparin. The HUVECs growing in the exponential phase were digested with pancreatin, and was adjust to have an appropriate level of cell density by using an F-12K complete medium containing 5% FBS, then 150 μL cells were inoculated into a 96-well plate at 3000 cells/well. 24 hours later, 50 μL of the test compound 4-fold diluted in a complete medium containing 5% FBS was added, and the same volume of a DMSO dilute solution was used as a control. After the cells were further cultured for 72 h, 20 μL MTS and 1 μL PMS were added to each well. 1-2 hours later, $OD_{490}$ was measured, with $OD_{650}$ as a reference. A dose-effect curve was drawn using the GraphPad Prism software, and half cytotoxic concentration ($CC_{50}$) was calculated. The therapeutic index (TI) of the test compound on HUVECs was calculated as $TI=CC_{50}/EC_{50}$.

The results showed that all the example compounds can significantly inhibit VEGF-stimulated proliferation of HUVECs, with activity lower than that of sunitinib. Some of the compounds (Compounds 2, 3, 5, 6, 8, 11, 13, 14 and 15), however, showed cytotoxicity to HUVEC considerably lower than that of sunitinib. The TIs of Compounds 2, 3, 5, 6, 8, 11, 14 and 15 were 2 to 3 times that of sunitinib, showing a bigger therapeutic window.

For Comparative compounds 1 and 2, because their N-containing heterocyclic ring on the far right side is attached to the carbonyl via a heteroatom, their TI is basically the same as sunitinib and is significantly lower than those of the compounds of the present invention. For Comparative compound 3, because its N-containing heterocyclic ring on the far right side is attached to the carbonyl via a methylene group, its TI is also basically the same as sunitinib and is significantly lower than those of the compounds of the present invention.

TABLE 2

Cytotoxicity to HUVEC, activity on VEGF-induced in vitro proliferation, and Therapeutic Index of some compounds.

| Compounds | $EC_{50}$ (nM) | $CC_{50}$ (nM) | $TI = CC_{50}/EC_{50}$ |
|---|---|---|---|
| 2 | 16.15 | >20000 | >1238 |
| 3 | 13.74 | >20000 | >1456 |
| 5 | 18.43 | >20000 | >1085 |
| 6 | 13.35 | 17566.77 | 1316 |
| 8 | 11.35 | >20000 | >1762 |
| 11 | 13.93 | >20000 | >1436 |
| 14 | 13.04 | >20000 | >1534 |
| 15 | 14.21 | 17732.12 | 1247 |
| Sunitinib | 7.73 | 4144.09 | 536 |
| Comparative compound 1 | 13.23 | 5689.26 | 430 |
| Comparative compound 2 | 12.31 | 6982.25 | 567 |
| Comparative compound 3 | 14.64 | 8054.61 | 550 |

Experimental Example 3

Assays for Inhibitory Activity on Proliferation of Human-Derived MV-4-11 Tumor Cell Line Human-derived acute leukemia cell line MV-4-11 is a cell line having mutation(s) in Flt-3. The in vitro anti-proliferation activity of the compounds on MV-4-11 was assayed by the MTS method: cells growing in the exponential phase were digested with pancreatin and counted; a suitable number of cells were re-suspended in a culture solution, added into a 96-well plate with 150 μL/well, and cultured overnight; a 50 μL culture solution containing 4-fold step-diluted test compound or a control was added to each well, followed by 72 h culturing; the culture solution was removed by pipetting, and 120 μL MTS assay solution (100 μL fresh media and 20 μL MTS solution) was added to each well, which was incubated at 37° C.; $OD_{490}$ was read; and the data were analyzed and processed using the GraphPad Prism5 software, to calculate $IC_{50}$.

The results showed that all the example compounds 1-15 had significant anti-proliferation activity on MV-4-11, and some of the compounds had activity similar to or higher than that of sunitinib (see the table below). FLT-3 (FMS-like tyrosine kinase 3) is a type III receptor tyrosine kinase, widely found in systems, the immune system, and the nervous system. Mutations in the FLT-3 gene and overexpression of FLT-3 would cause tumorigenesis. The specific anti-proliferation activity of Compounds 1-15 on MV-4-11 also indicates that the example compounds are similar to sunitinib as an FLT-3 inhibitor.

TABLE 3

| Inhibition of some compounds on in vitro proliferation of human-derived MV-4-11 cell line. | | |
|---|---|---|
| Compounds | $IC_{50}$ (nM) | Maximum inhibition (%) |
| 2 | 4.70 | 92.6 |
| 3 | 10.67 | 92.1 |
| 5 | 1.68 | 95.0 |
| 6 | 11.58 | 92.4 |
| 9 | 5.34 | 94.3 |
| 12 | 7.87 | 93.1 |
| 13 | 6.41 | 90.2 |
| 15 | 12.34 | 92.5 |
| Sunitinib | 3.94 | 94.4 |

Experimental Example 4

In Vivo Inhibition on MV-4-11 Transplanted Tumor in Nude Mice

MV-4-11 cells were cultured to proliferate in vitro, and the cells growing in the exponential phase were harvested and re-suspended in a serum-free EMEM culture medium. The cell suspension was subcutaneously injected by a syringe into the axillary cavity of the right forelimb of male Balb/c nude mice. The animals and growth of transplanted tumors were observed regularly. When the tumor volume grew to about 100 to 300 $mm^3$, animals having tumors of a suitable size were selected and randomized into groups with 6 animals per group. Each group was intragastrically administrated with a blank vehicle (0.5% CMC) or a suspension of the example Compound 6 or sunitinib at a dose of 80 mg/kg, once per day, for an administration period of 3 weeks. During the administration period, the diameter of tumors and body weight (BW) of animals were measured, and the living status of animals was monitored. The experiment was finished 3 weeks after administration, and the animals were sacrificed with $CO_2$ and subjected to autopsy.

Tumor volume (TV) was calculated by the equation $TV=\frac{1}{2} \times a \times b^2$, wherein a is the longer diameter of the tumor, and b is the shorter diameter of the tumor.

The results showed that on day 21 of intragastric administration, the tumors in the vehicle control group had grown to nearly 6 times the volume of the original, while the tumors in the groups treated with Compound 6 had completely disappeared, and Compound 6 had no significant impact on the body weight of animals. Although sunitinib also showed noticeable anti-tumor effect in that most animals had their tumors disappeared, the body weight of the animals are significantly reduced and the toxicity was evident.

TABLE 4

Inhibition of Compound 6 on MV-4-11 transplanted tumor in nude mice.

| Group | Number of animals Initial/End | Dose (mg/kg) | $D_0$ TV | $D_0$ BW | $D_{21}$ TV | $D_{21}$ BW |
|---|---|---|---|---|---|---|
| Vehicle control | 6/6 | — | 243.76 ± 20.1 | 19.42 ± 0.08 | 1443.81 ± 246.22 | 22.67 ± 0.48 |
| Sunitinib | 6/6 | 80 | 242.75 ± 20.58 | 19.47 ± 0.33 | 12.97 ± 2.47** | 16.02 ± 0.56** |
| Compound 6 | 6/6 | 80 | 238.25 ± 13.18 | 20.42 ± 0.20 | 0.00 ± 0.00** | 21.38 ± 0.37 |

**P < 0.01 as compared to the vehicle control

As can be seen from the results of experiments on MV-4-11 transplanted tumor in nude mice, Compound 6 of the present invention has a very good inhibitory effect on MV-4-11 transplanted tumors, in that a dose of 80 mg/kg can lead to complete disappearance of tumors and has little impact on the body weight. Sunitinib significantly reduces the body weight of animals and shows obvious toxicity. These results demonstrate that the compounds of the present invention have an anti-tumor effect comparable to that of sunitinib, but have lower toxicity, a bigger therapeutic window, and a higher value in drug development.

The invention claimed is:

1. A pyrrole-substituted indolone derivative with a structure shown in general formula (I) below, or having a structure represented by Compound 4, Compound 6, Compound 7, Compound 8, Compound 9, or Compound 15 below or pharmaceutically acceptable salts thereof:

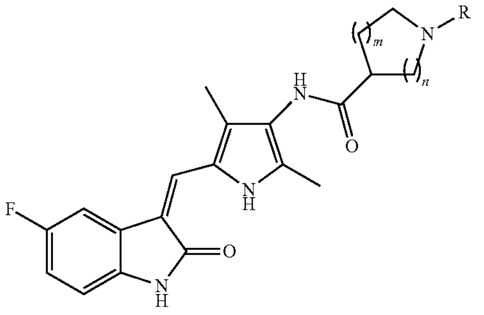

(I)

wherein m is selected from 0, 1 and 2;

n is selected from 1, 2 and 3; and

R is selected from hydrogen, a $C_1$-$C_6$ linear or branched alkyl, a $C_3$-$C_7$ cycloalkyl, formyl substituted with a $C_1$-$C_6$ linear or branched alkyl, $C_3$-$C_7$ cycloalkylformyl, t-butoxycarbonyl, substituted carbamoyl, or a 5- to 7-membered cyclic carbamoyl;

4

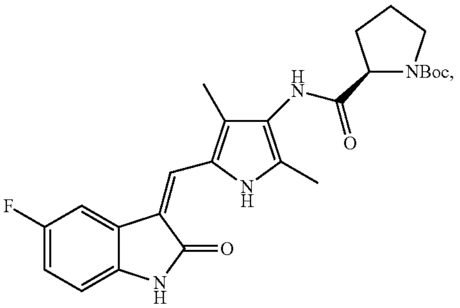

6

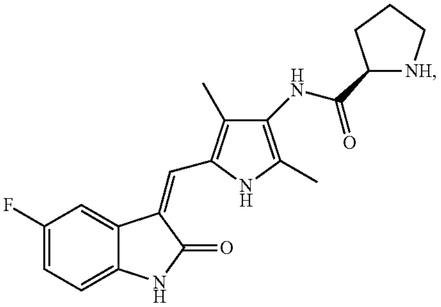

7

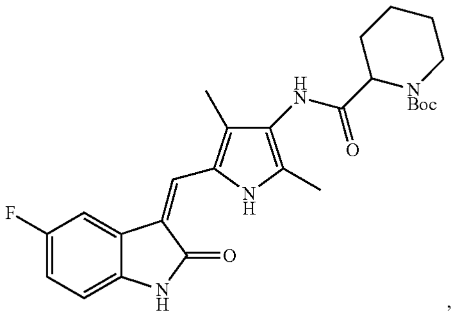

,

8

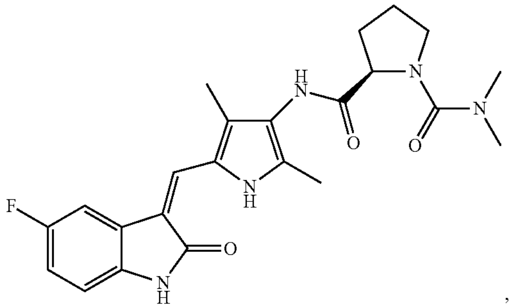

,

9

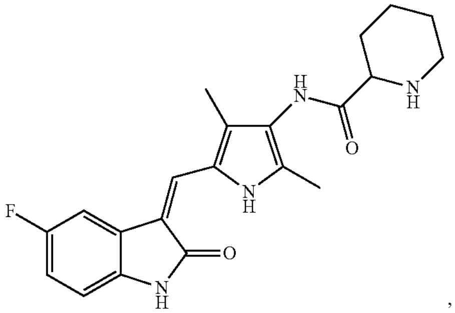

,

-continued

15

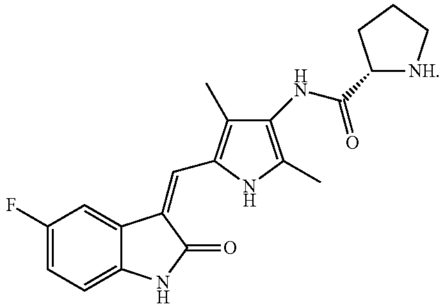

2. The pyrrole-substituted indolone derivative according to claim 1, wherein R is selected from hydrogen, a $C_1$-$C_3$ linear or branched alkyl, a $C_4$-$C_6$ cycloalkyl, formyl substituted with a $C_1$-$C_3$ linear or branched alkyl, $C_3$-$C_6$ cycloalkylformyl, t-butoxycarbonyl, N,N-dimethyl carbamoyl, N,N-diethyl carbamoyl, N,N-dipropyl carbamoyl, pyrrolidin-1-ylformyl, or piperidin-1-ylformyl.

3. The pyrrole-substituted indolone derivative according to claim 1, wherein R is selected from hydrogen, methyl, t-butoxycarbonyl, N,N-dimethyl carbamoyl, or pyrrolidin-1-ylformyl.

4. The pyrrole-substituted indolone derivative according to claim 1, wherein the pyrrole-substituted indolone derivative with a structure shown in general formula (I) is selected from Compounds 1 to 3, 5, and 10 to 14 below:

1

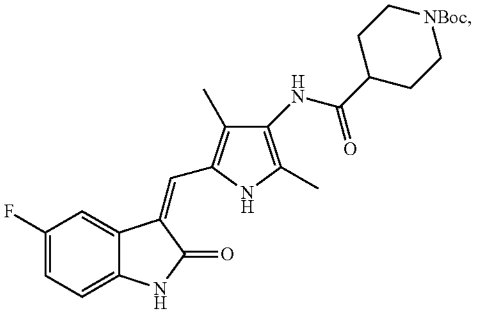

2

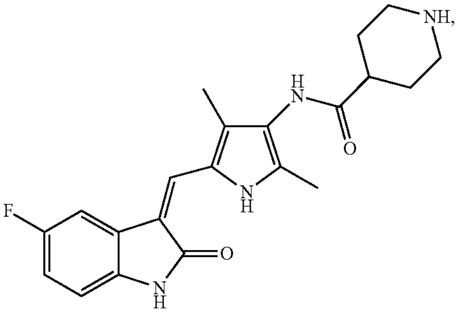

-continued

3

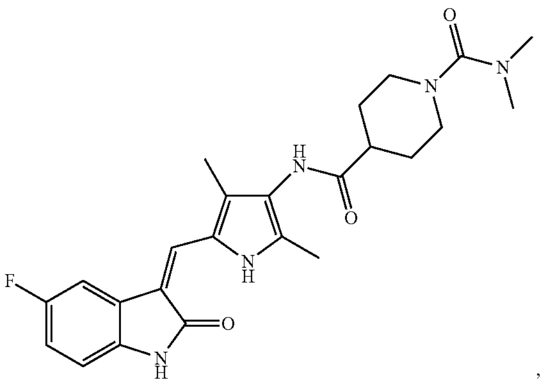

,

5

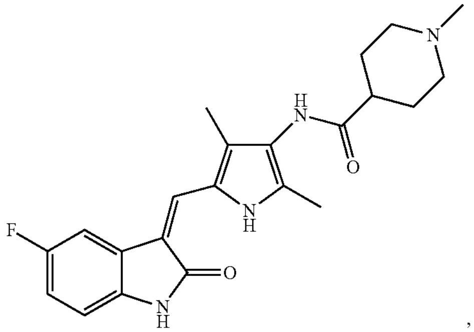

,

10

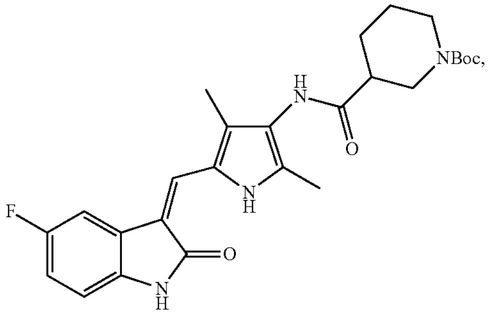

11

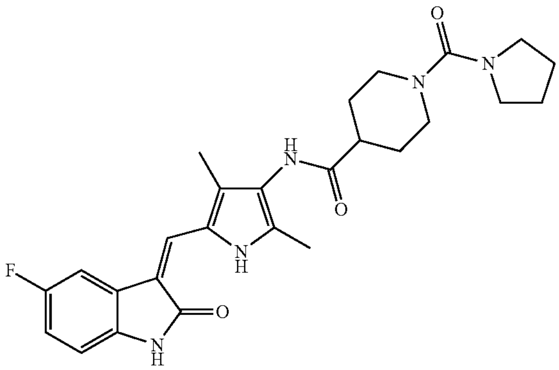

,

-continued

12

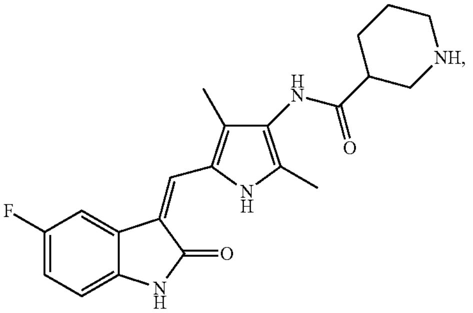

13

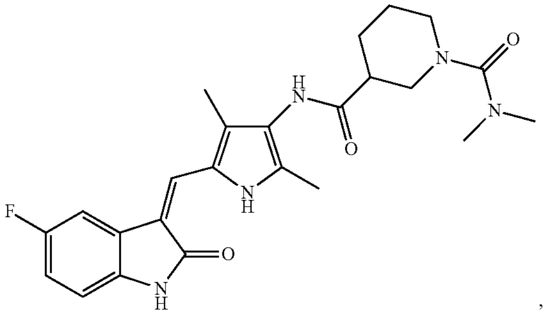

, or

14

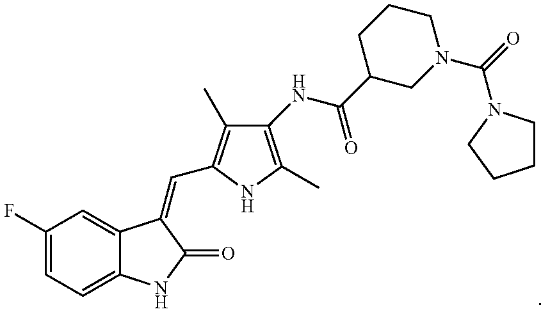

.

5. The pyrrole-substituted indolone derivative or pharmaceutically acceptable salts thereof according to claim 1, wherein the salts are hydrochlorides.

6. A pharmaceutical composition, comprising:

a therapeutically effective amount for treating receptor tyrosine kinase-mediated diseases of one or more pyrrole-substituted indolone derivatives or pharmaceutically acceptable salts thereof according to claim 1, and optionally auxiliaries.

7. A method for treating receptor tyrosine kinase-mediated tumors in a mammal comprising administering a therapeutically effective amount of one or more of the pyrrole-substituted indolone derivatives or pharmaceutically acceptable salts thereof according to claim 1.

8. The method according to claim 7, comprising administering a therapeutically effective amount of a pyrrole-substituted indolone derivative selected from Compounds 1 to 3, 5, and 10 to 14 below:

1
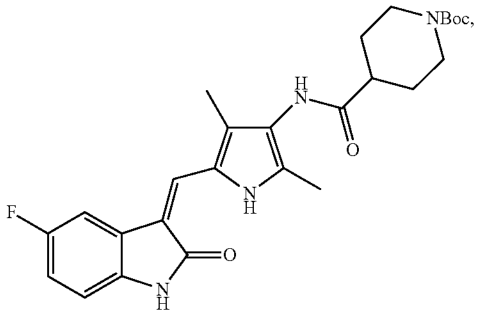
2
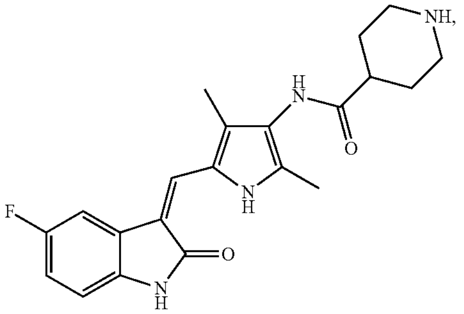
3
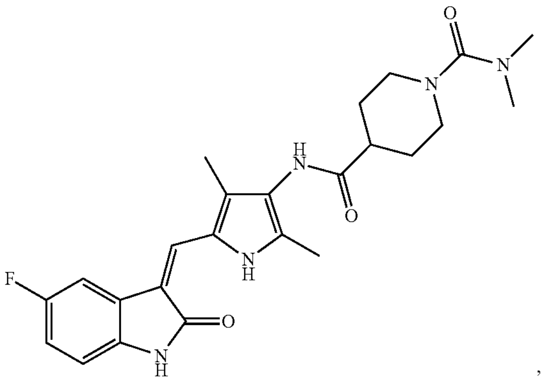
,
5
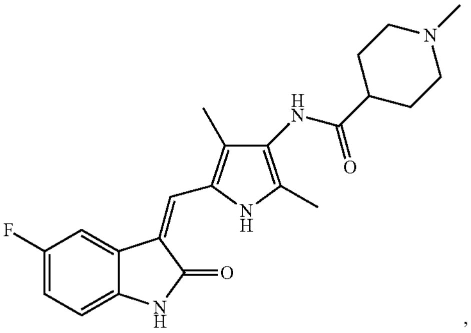
,
-continued
10
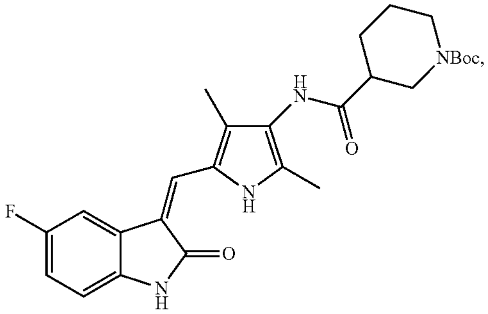
11
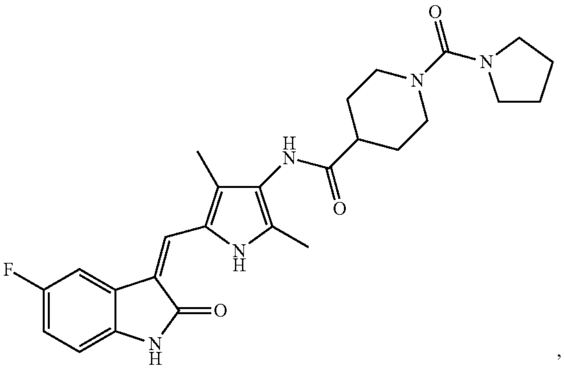
,
12
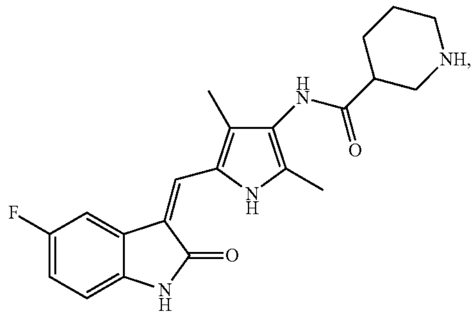
13
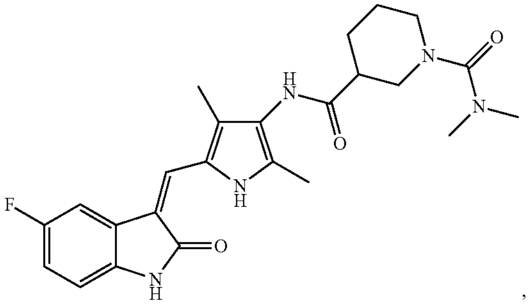
, and -continued

14

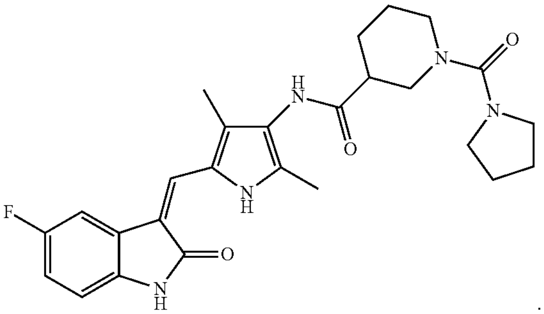

.

9. The method according to claim 7, wherein R is selected from hydrogen, a C1-C3 linear or branched alkyl, a C4-C6 cycloalkyl, formyl substituted with a C1-C3 linear or branched alkyl, C3-C6 cycloalkylformyl, t-butoxycarbonyl, N,N-dimethyl carbamoyl, N,N-diethyl carbamoyl, N,N-dipropyl carbamoyl, pyrrolidin-1-ylformyl, or piperidin-1-ylformyl.

10. The method according to claim 7, wherein R is selected from hydrogen, methyl, t-butoxycarbonyl, N,N-dimethyl carbamoyl, or pyrrolidin-1-ylformyl.

11. A method for inhibiting tumor cell proliferation and/or migration driven by receptor tyrosine kinases in a mammal comprising administering a therapeutically effective amount of one or more of the pyrrole-substituted indolone derivatives or pharmaceutically acceptable salts thereof according to claim 1.

12. The method according to claim 11, comprising administering a therapeutically effective amount of a pyrrole-substituted indolone derivative selected from Compounds 1 to 3, 5, and 10 to 14 below:

1

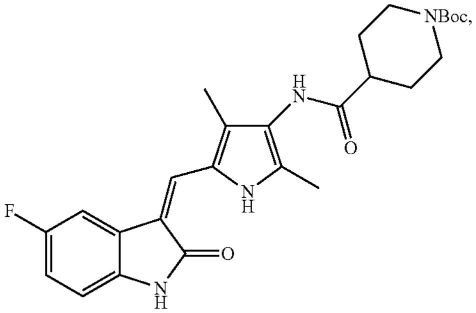

2

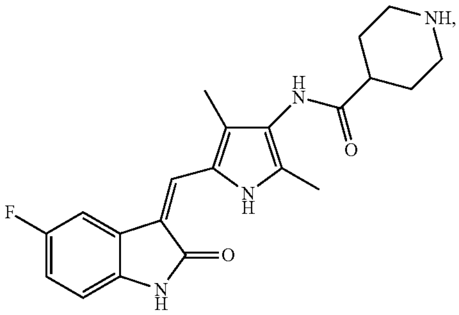

-continued

3

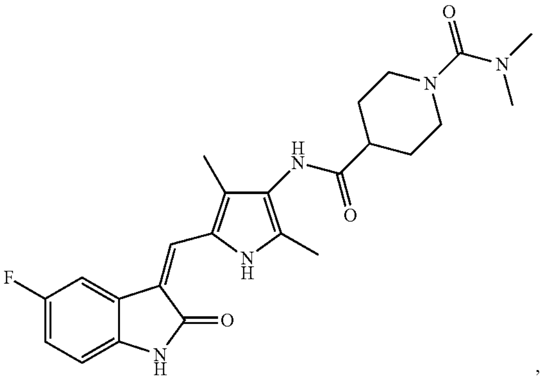

,

5

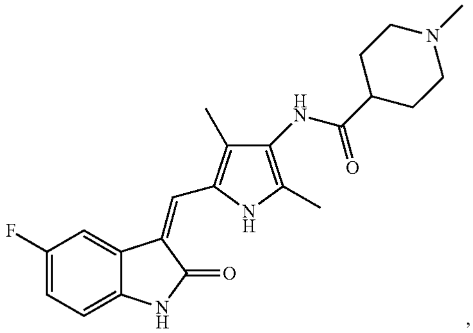

,

10

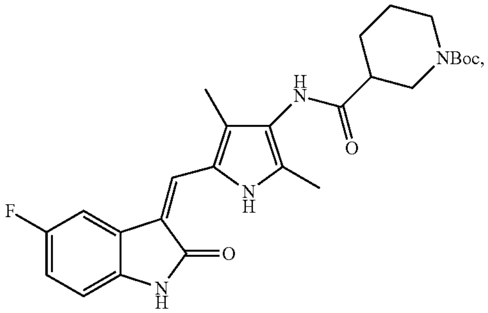

11

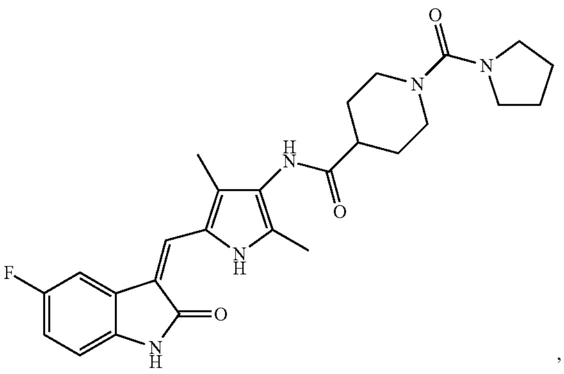

,

-continued

12

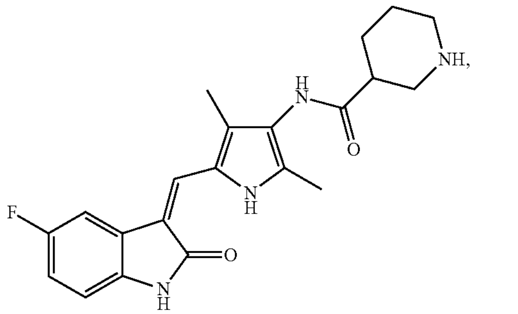

13

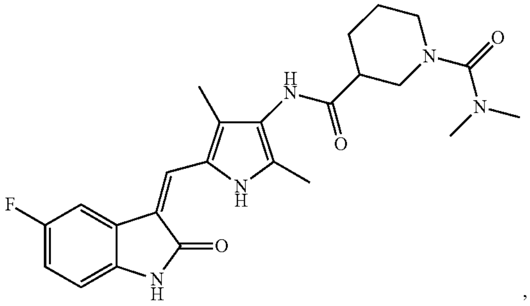

, and

14

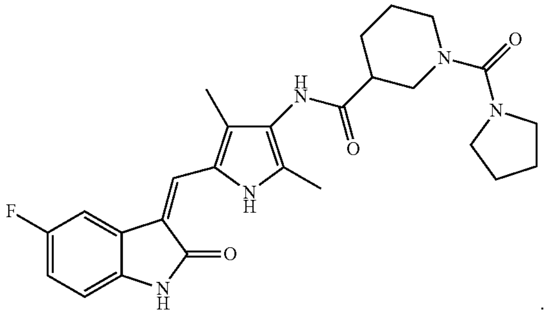

.

13. The method according to claim 11, wherein R is selected from hydrogen, a C1-C3 linear or branched alkyl, a C4-C6 cycloalkyl, formyl substituted with a C1-C3 linear or branched alkyl, C3-C6 cycloalkylformyl, t-butoxycarbonyl, N,N-dimethyl carbamoyl, N,N-diethyl carbamoyl, N,N-dipropyl carbamoyl, pyrrolidin-1-ylformyl, or piperidin-1-ylformyl.

14. The method according to claim 11, wherein R is selected from hydrogen, methyl, t-butoxycarbonyl, N,N-dimethyl carbamoyl, or pyrrolidin-1-ylformyl.

15. A method for treating receptor tyrosine kinase-mediated diseases in a mammal comprising administering a therapeutically effective amount of one or more of the pyrrole-substituted indolone derivatives or pharmaceutically acceptable salts thereof according to claim 1.

16. The method according to claim 15, comprising administering a therapeutically effective amount of a pyrrole-substituted indolone derivative selected from Compounds 1 to 3, 5, and 10 to 14 below:

1

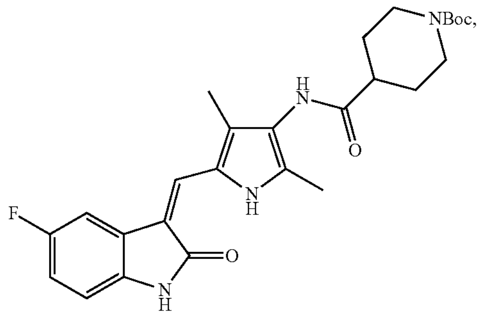

2

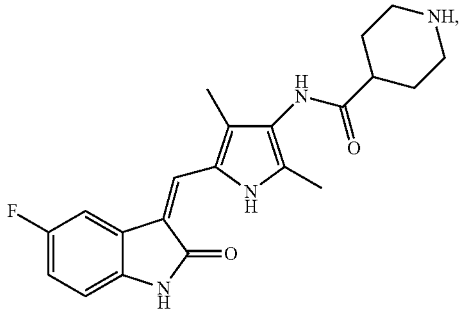

3

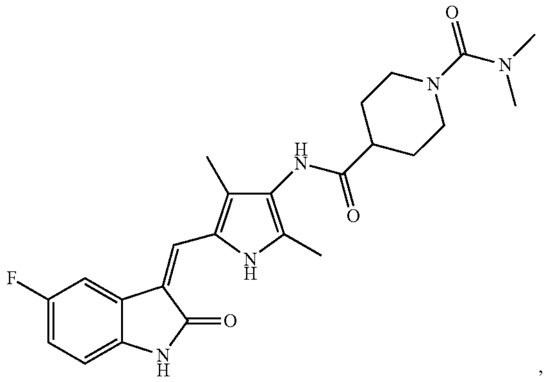

,

5

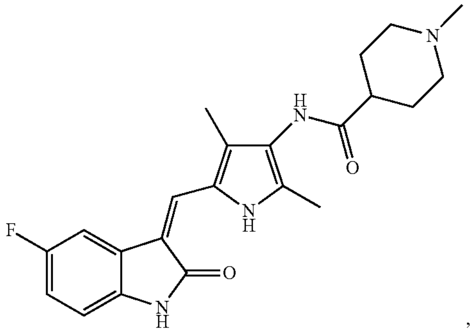

,

-continued

10

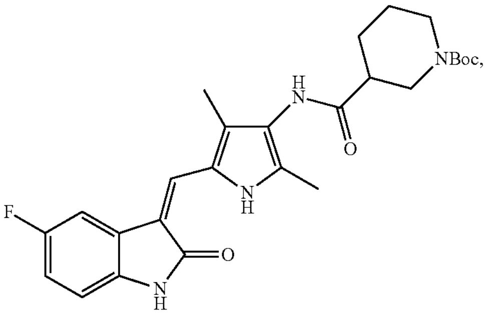

11

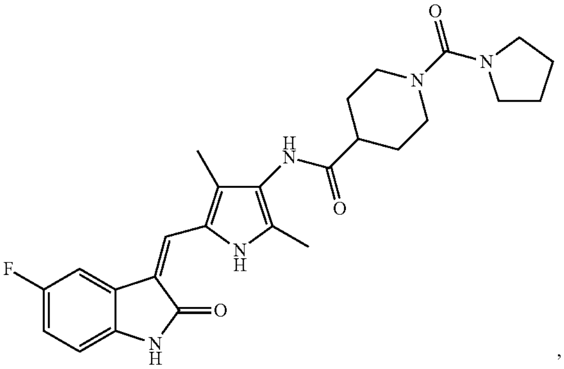

,

12

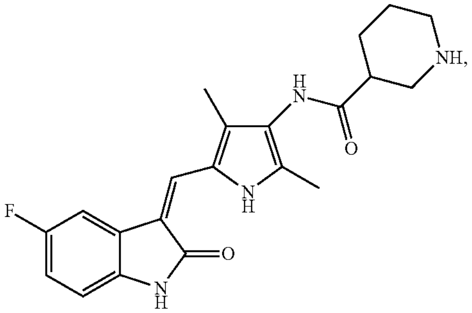

-continued

13

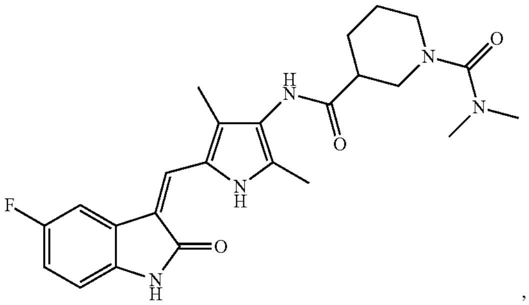

, and

14

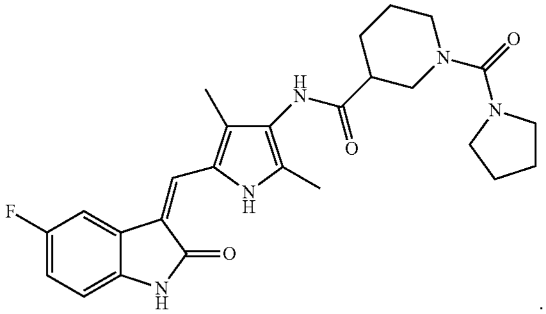

.

17. The method according to claim 15, wherein R is selected from hydrogen, a C1-C3 linear or branched alkyl, a C4-C6 cycloalkyl, formyl substituted with a C1-C3 linear or branched alkyl, C3-C6 cycloalkylformyl, t-butoxycarbonyl, N,N-dimethyl carbamoyl, N,N-diethyl carbamoyl, N,N-dipropyl carbamoyl, pyrrolidin-1-ylformyl, or piperidin-1-ylformyl.

18. The method according to claim 15, wherein R is selected from hydrogen, methyl, t-butoxycarbonyl, N,N-dimethyl carbamoyl, or pyrrolidin-1-ylformyl.

19. The method according to claim 15, wherein the mammal is human.

20. The method according to claim 7, wherein the mammal is human.

* * * * *